US011992509B2

United States Patent
Kim

(10) Patent No.: US 11,992,509 B2
(45) Date of Patent: May 28, 2024

(54) **COMPOSITION FOR PREVENTION OR TREATMENT OF NEURODEVELOPMENTAL DISORDER, NEUROLOGIC DISEASES, OR PSYCHIATRIC DISEASES COMPRISING EXTRACELLULAR VESICLES DERIVED FROM *MICROCOCCUS LUTEUS***

(71) Applicant: MD HEALTHCARE INC., Seoul (KR)

(72) Inventor: Yoon-Keun Kim, Paju-Si (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 17/646,143

(22) Filed: Dec. 27, 2021

(65) Prior Publication Data
US 2022/0202878 A1 Jun. 30, 2022

(30) Foreign Application Priority Data
Dec. 28, 2020 (KR) .................. 10-2020-0184337

(51) Int. Cl.
*A61K 35/74* (2015.01)
*A61P 25/28* (2006.01)

(52) U.S. Cl.
CPC .............. *A61K 35/74* (2013.01); *A61P 25/28* (2018.01)

(58) Field of Classification Search
CPC ....... A61K 35/74; A61K 9/0073; A61P 25/28; A61P 1/16; A61P 11/00; A61P 13/12; A61P 29/00; A61P 35/00; A61P 37/08; A23L 33/135; A23V 2002/00
See application file for complete search history.

(56) References Cited

U.S. PATENT DOCUMENTS

| | | | |
|---|---|---|---|
| 2019/0070225 A1 | 3/2019 | Strandwitz et al. | |
| 2020/0254028 A1* | 8/2020 | Goodman | A61K 35/74 |

FOREIGN PATENT DOCUMENTS

| | | |
|---|---|---|
| KR | 10-2018-0019482 A | 2/2018 |
| KR | 10-2019-0103962 A | 9/2019 |
| KR | 10-2020-0053531 A | 5/2020 |

OTHER PUBLICATIONS

Schmidt et al., Neurodegenerative Diseases of the Retina and Potential for Protection and Recovery, Current Neuropharmacology, vol. 6, p. 164-178. (Year: 2008).*
Han et al., Current Opinion on the Role of Neurogenesis in the Therapeutic Strategies for Alzheimer Disease, Parkinson Disease, and Ischemic Stroke; Considering Neuronal Voiding Function, International Neurourology Journal, vol. 20, p. 276-287. (Year: 2016).*
Guan et al., Key Mechanisms and Potential Targets of the NLRP3 Inflammasome in Neurodegenerative Diseases, Frontiers in Integrative Neuroscience, vol. 14, p. 1-9. (Year: 2020).*
https://www.nia.nih.gov/health/what-is-dementia#:~:text=Who%20can%20diagnose%20dementia%3F,often%20consulted%20to%20diagnose%20dementia (Year: 2022).*
https://www.jax.org/strain/025971 (Year: 2022).*
Izadpanah M, Dargahi L, Ai J, et al. Extracellular Vesicles as a Neprilysin Delivery System Memory Improvement in Alzheimer's Disease. Iranian Journal of Pharmaceutical Research Spring 2020;19(2):45-60. (Year: 2020).*
Kumar et al., Challenges in Biomaterial-Based Drug Delivery Approach for the Treatment of Neurodegenerative Diseases: Opportunities for Extracellular Vesicles, International Journal of Molecular Sciences, Dec. 25, 2020, p. 1-21 (Year: 2020).*
Choi et al., "Extracellular Vesicles Derived from Lactobacillus plantarum Increase BDNF Expression in Cultured Hippocampal Neurons and Produce Antidepressant-like Effects in Mice", Exp Neurobiol, 2019, vol. 28, No. 2, pp. 158-171.
International Search Report for PCT/KR2021/016633, 5 pages, dated Feb. 21, 2022.

* cited by examiner

*Primary Examiner* — Adam Weidner
*Assistant Examiner* — Tiffany M Gough
(74) *Attorney, Agent, or Firm* — Vorys, Sater, Seymour and Pease LLP; Mih Suhn Koh

(57) ABSTRACT

Provided is a method for alleviating, preventing or treating a neurodevelopmental disease, neurologic disease, or psychiatric disease, comprising administering to a subject in need thereof a composition including, as an active ingredient, vesicle derived from *Micrococcus luteus*, wherein the disease including Alzheimer's disease, Parkinson's disease, amyotropic lateral sclerosis, Huntington's disease, epilepsy, multiple sclerosis, chronic inflammatory demyelinating polyneuropathy, diabetic neuropathy, autism spectrum disorder, attention deficit hyperactivity syndrome, major depressive disorder, bipolar disorder, anxiety disorders, schizophrenia, obsessive compulsive disorder, post-traumatic stress disorder, dissociative disorders, eating disorders, substance use disorder, and personality disorders occurring as a result of neurogenesis dysfunction or neuroinflammation.

5 Claims, 23 Drawing Sheets
Specification includes a Sequence Listing.

COMPOSITION FOR PREVENTION OR TREATMENT OF NEURODEVELOPMENTAL DISORDER, NEUROLOGIC DISEASES, OR PSYCHIATRIC DISEASES COMPRISING EXTRACELLULAR VESICLES DERIVED FROM *MICROCOCCUS LUTEUS*

TECHNICAL FIELD

The present invention relates to extracellular vesicles derived from *Micrococcus luteus* and a use thereof, and more particularly, to a composition for preventing or treating a neurodevelopmental disease, a neurologic disease or a psychiatric disease, which comprises extracellular vesicles derived from *Micrococcus luteus* as an active ingredient.

This application claims priority to and the benefit of Korean Patent Application Nos. 10-2020-0184337 and 10-2021-0156079 filed in the Korean Intellectual Property Office on Dec. 28, 2020 and Nov. 12, 2021, respectively, and all the contents disclosed in the specification and drawings of the applications are incorporated in this application.

SEQUENCE LISTING

The Sequence Listing submitted in text format (.txt) filed on Dec. 27, 2021, named "SequenceListing.txt", created on Dec. 27, 2021 (4.87 KB), is incorporated herein by reference.

BACKGROUND ART

As the 21st century begins, the importance of an acute infectious disease that used to be recognized as a communicable disease in the past has decreased, whereas a chronic inflammatory disease caused by an immune or metabolic disorder in the major organs of our body has changed the pattern of diseases as a major disease that reduces the quality of life and determines the human's life expectancy. In recent years, studies have focused on the fact that an intractable disease occurs because disharmony between a human and microbiome causes abnormalities in immune and metabolic functions, resulting in chronic inflammation and abnormal cell death. In particular, as an intractable disease in the aging society of the 21st century, a neurologic disease including cognitive dysfunction such as Alzheimer's disease and motor dysfunction such as Parkinson's disease and Lou Gehrig's disease; a neurodevelopmental disorder such as autism and an attention-deficit hyperactivity disorder; a psychiatric disease such as an anxiety disorder, depression, and schizophrenia, and the like have become major problems for national health as major diseases that determine the quality of human life.

Neurodegeneration of nerve cells (neurons) leads to abnormalities in the structure and function of brain-nerve tissues due to the abnormal death of nerve cells. A neurologic disease, such as Alzheimer's disease, Parkinson's disease, amyotropic lateral sclerosis, Huntington's disease, epilepsy, multiple sclerosis, chronic inflammatory demyelinating polyneuropathy, and diabetic neuropathy, occurs as a result of neurodegeneration or neuroinflammation of nerve cells. Further, neurologic diseases such as Kearns-Sayre syndrome (KSS), chronic progressive external ophthalmoplegia (CPEO), mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), Leigh syndrome (LS), and mitochondrial recessive ataxia syndrome are also caused by degenerative changes in nerve cells.

Recently, it has been revealed that mental disorders such as depression, autism, and schizophrenia are closely associated with abdominal pain. Abdominal pain is accompanied by diarrhea and constipation, and leads to irritable bowel syndrome when repeated, which has been shown to be associated with gut microbial dysbiosis. It has been reported that when an intestinal bacterial imbalance occurs due to bad food, antibiotic use, and the like, harmful intestinal microorganisms cause cracks in the healthy large intestine defense membrane, causing intestinal leakage, and then toxins derived from harmful bacteria are absorbed systemically, causing or exacerbating depression [Pharmacotherapy. 2015 October; 35(10): 910-6].

As the results of many studies on the pathogenesis of a neurodevelopmental disease, a neurologic disease and a psychiatric disease have been recently published, it has been revealed that there are problems in key pathways of these diseases at the molecular level. Discovering and recovering the key etiological mechanisms associated with the pathogenesis of a disease gives hope that many diseases can be treated at the same time. Cellular senescence occurs while cells are repeatedly exposed to various stresses, and when the immune and metabolic functions of cells are impaired during this process, the cells undergo abnormal apoptosis. That is, the key pathophysiology of a neurologic disease, a neurodevelopmental disease, and a psychiatric disease occurs as a result of abnormal death of neural stem cells or an inter-neuronal integrity disorder.

Energy metabolism creates the energy required to carry out functions of cells and produces various materials, thereby making proteins and lipids from the endoplasmic reticulum (ER) through ATP produced by mitochondria and supplying the proteins and lipids to a required region. Cells face a variety of stresses from the moment when they are formed, and biological, chemical, physical or psychological stress induces endoplasmic reticulum (ER) stress, mitochondrial dysfunction, lysosomal damage, and the like in cells, thereby producing abnormal materials in cells, and cells induce an inflammatory response by recognizing the abnormal material as a danger signal.

Immunity is a cellular defense mechanism against biological, chemical, physical and mental stress, and occurs through innate immunity and adaptive immunity. Recently, it has been found that in relation with the etiology of inflammatory diseases due to immune dysfunction, danger signals resulting from intracellular oxidative stress are recognized by a nucleotide-binding oligomerization domain (NLRP) which is a pattern recognition receptor (PRR) in the cytoplasm, and among them, a NLRP3 protein forms an inflammasome to cause an inflammatory response and abnormal cell death. In particular, inflammation caused by activation of the NLRP3 inflammasome has become known as the key etiological mechanism of various neurodevelopmental, neurological, and psychiatric diseases.

It is known that the number of microorganisms that coexist in the human body reaches 100 trillion, which is about 10-fold larger than that of human cells, and the number of genes of microorganisms is 100-fold larger than that of humans. A microbiota or microbiome refers to a microbial community including bacteria, archaea and eukarya present in a given habitat.

Bacteria that coexist in our bodies and bacteria that exist in the surrounding environment secrete nanometer-sized vesicles to exchange information such as genes, low molecular compounds, and proteins with other cells. The mucosa forms a physical defense membrane through which particles having a size of 200 nanometers (nm) or more cannot pass, so that bacteria coexisting in the mucosa cannot pass through the mucosa, but bacteria-derived vesicles have a size of 200 nanometers or less, and thus relatively freely pass through epithelial cells via the mucosa to be absorbed in our bodies. As described above, although bacteria-derived vesicles are secreted from bacteria, they differ from bacteria in terms of their constituents, absorption rate in the body, and risk of side effects, and therefore, the use of bacteria-derived vesicles is completely different from that of living cells or has a significant effect.

Locally secreted bacteria-derived vesicles are absorbed through the epithelial cells of the mucosa to induce a local inflammatory response, and vesicles that have passed through the epithelial cells are systemically absorbed through a lymphatic vessel to be distributed to respective organs, and regulate immune and inflammatory responses in the distributed organs. For example, vesicles derived from pathogenic gram-negative bacteria such as *Escherichia coli* are pathogenic nanoparticles that cause local colitis, are absorbed in vascular endothelial cells when absorbed by blood vessels to promote a systemic inflammatory response and blood coagulation by inducing an inflammatory response, and are also absorbed in muscle cells where insulin acts to cause insulin resistance and diabetes mellitus. In contrast, vesicles derived from beneficial bacteria may regulate a disease by regulating immune and metabolic dysfunctions caused by pathogenic vesicles.

*Micrococcus luteus* refers to gram-positive bacteria belonging to the genus *Micrococcus*, which is widely distributed in nature, such as water, dust, and soil. These bacteria are known to produce riboflavin when grown in toxic organic pollutants such as pyridine, and absorb UV light by the lutein pigment. These bacteria are also known to be isolated from dairy products and beer, grown in a dry environment or high-salt environment, and survive for a long time at a refrigeration temperature, for example in a refrigerator, although not forming spores.

However, there has been no report in which vesicles derived from *Micrococcus luteus* are applied to the treatment of a neurodevelopmental disease, a neurologic disease or a psychiatric disease to date.

DISCLOSURE

Technical Problem

The inventors have earnestly studied to solve the conventional problems, confirming that, when cells were treated with vesicles derived from *Micrococcus luteus*, the vesicles not only significantly inhibit the secretion of an inflammatory mediator by pathogenic factor, but also efficiently inhibit abnormal immune function by a biological pathogenic factor. Further, the present inventors confirmed that vesicles derived from *Micrococcus luteus* regulate immune functions by suppressing the expression of a NLRP3 protein associated with the etiology of various diseases and the secretion of inflammatory mediators by NLRP3 inflammasome formation. In addition, the present inventors confirmed that the vesicles enhance homeostasis by activating endothelial NO synthase (eNOS), which is an important signal for cell homeostasis. Furthermore, the present inventors confirmed that when a mouse model of a brain disease which causes cognitive dysfunction by excessively inducing the death of nerve cells is treated with the vesicles, not only behavioral disorders associated with cognitive function, but also abnormal protein deposition are suppressed. Further, the present inventors confirmed that in the brain disease mouse model, vesicles derived from *Micrococcus luteus* exhibit a therapeutic effect on a neurodevelopmental disease, a neurologic disease, or a psychiatric disease by enhancing the proliferation and differentiation of neural stem cells, and inter-neuronal integrity. In addition, the present inventors confirmed that vesicles derived from *Micrococcus luteus* act on nerve cells to enhance the expression of a brain-derived neurotrophic factor (BDNF) which induces neurogenesis and a sirtuin protein which prevents cellular senescence caused by stress, and as a result, a therapeutic effect by neurogenesis occurs, thereby completing the present invention based on this.

Thus, an object of the present invention is to provide a pharmaceutical composition for preventing or treating a neurodevelopmental disease, a neurologic disease, or a psychiatric disease, comprising vesicles derived from *Micrococcus luteus* as an active ingredient.

In addition, another object of the present invention is to provide a food composition for preventing or alleviating a neurodevelopmental disease, a neurologic disease, or a psychiatric disease, comprising vesicles derived from *Micrococcus luteus* as an active ingredient.

In addition, another object of the present invention is to provide an inhalant composition for preventing or treating a neurodevelopmental disease, a neurologic disease, or a psychiatric disease, comprising vesicles derived from *Micrococcus luteus* as an active ingredient.

In addition, another object of the present invention is to provide a composition for delivering a drug for treating a neurodevelopmental disease, a neurologic disease, or a psychiatric disease, comprising vesicles derived from *Micrococcus luteus* as an active ingredient.

In addition, another object of the present invention is to provide an anti-aging pharmaceutical composition, comprising vesicles derived from *Micrococcus luteus* as an active ingredient.

In addition, another object of the present invention is to provide an anti-aging food composition, comprising vesicles derived from *Micrococcus luteus* as an active ingredient.

In addition, another object of the present invention is to provide a pharmaceutical composition for preventing or treating a neurodevelopmental disease, a neurologic disease, or a psychiatric disease, comprising vesicles derived from bacteria of the genus *Micrococcus* as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a pharmaceutical composition for preventing or treating a neurodevelopmental disease, a neurologic disease, or a psychiatric disease, comprising vesicles derived from *Micrococcus luteus* as an active ingredient.

In addition, the present invention provides a food composition for preventing or alleviating a neurodevelopmental disease, a neurologic disease, or a psychiatric disease, comprising vesicles derived from *Micrococcus luteus* as an active ingredient.

In addition, the present invention provides an inhalant composition for preventing or treating a neurodevelopmental disease, a neurologic disease, or a psychiatric disease, comprising vesicles derived from *Micrococcus luteus* as an active ingredient.

In addition, the present invention provides a composition for delivering a drug for treating a neurodevelopmental disease, a neurologic disease, or a psychiatric disease, comprising vesicles derived from *Micrococcus luteus* as an active ingredient.

In addition, the present invention provides an anti-aging pharmaceutical composition, comprising vesicles derived from *Micrococcus luteus* as an active ingredient.

In addition, the present invention provides an anti-aging food composition, comprising vesicles derived from *Micrococcus luteus* as an active ingredient.

In addition, the present invention provides a pharmaceutical composition for preventing or treating a neurodevelopmental disease, a neurologic disease, or a psychiatric disease, comprising vesicles derived from bacteria of the genus *Micrococcus* as an active ingredient.

As an exemplary embodiment of the present invention, the neurologic disease may be a degenerative neurologic disease or an inflammatory neurologic disease, but the present invention is not limited thereto.

As another exemplary embodiment of the present invention, the degenerative neurologic disease may be one or more diseases selected from the group consisting of Alzheimer's disease, Parkinson's disease, amyotropic lateral sclerosis, Huntington's disease, epilepsy, Kearns-Sayre syndrome (KSS), chronic progressive external ophthalmoplegia (CPEO), mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), Leigh syndrome (LS), and mitochondrial recessive ataxia syndrome, but the present invention is not limited thereto.

As another exemplary embodiment of the present invention, the inflammatory neurologic disease may be one or more diseases selected from the group consisting of multiple sclerosis, chronic inflammatory demyelinating polyneuropathy, and diabetic neuropathy, but the present invention is not limited thereto.

As another exemplary embodiment of the present invention, the psychiatric disease may be one or more diseases selected from the group consisting of major depressive disorder, bipolar disorder, anxiety disorders, schizophrenia, obsessive compulsive disorder, post-traumatic stress disorder, dissociative disorders, eating disorders, substance use disorder, and personality disorders, but the present invention is not limited thereto.

As another exemplary embodiment of the present invention, the anxiety disorder may be one or more anxiety disorders selected from the group consisting of panic disorders, social anxiety disorders, generalized anxiety disorders, and specific phobias, but the present invention is not limited thereto.

As another exemplary embodiment of the present invention, the personality disorder may be one or more personality disorders selected from the group consisting of paranoid personality disorder, antisocial personality disorder, borderline personality disorder, narcissistic personality disorder, avoidant personality disorder, and dependent personality disorder, but the present invention is not limited thereto.

As another exemplary embodiment of the present invention, the neurodevelopmental disease may be one or more selected from the group consisting of intellectual disabilities, communication disorders, autism spectrum disorders, attention deficit hyperactivity disorders, specific learning disorders, and motor disorders, but the present invention is not limited thereto.

As another exemplary embodiment of the present invention, the neurodevelopmental disease, neurologic disease, or psychiatric disease may be due to neurogenesis dysfunction, but is not limited thereto.

As another exemplary embodiment of the present invention, the neurodevelopmental disease, neurologic disease, or psychiatric disease may be mediated by a NLR family pyrin domain containing 3 inflammasome (NLRP3 inflammasome), but is not limited thereto.

As another exemplary embodiment of the present invention, the composition may suppress NLRP3 inflammasome formation, but is not limited thereto.

As another exemplary embodiment of the present invention, the vesicles may have an average diameter of 10 to 200 nm, but the present invention is not limited thereto.

As another exemplary embodiment of the present invention, the vesicles may be naturally secreted or artificially produced from *Micrococcus luteus*, but the present invention is not limited thereto.

As another exemplary embodiment of the present invention, the composition may suppress the aging of brain or nerve cells, but is not limited thereto.

In addition, the present invention provides a method for preventing or treating a neurodevelopmental disease, a neurologic disease, or a psychiatric disease, the method comprising administering a composition comprising vesicles derived from *Micrococcus luteus* as an active ingredient to a subject in need thereof.

In addition, the present invention provides a use of a composition comprising vesicles derived from *Micrococcus luteus* as an active ingredient for preventing or treating a neurodevelopmental disease, a neurologic disease, or a psychiatric disease.

In addition, the present invention provides a use of vesicles derived from *Micrococcus luteus* for preparing a drug for treating a neurodevelopmental disease, a neurologic disease, or a psychiatric disease.

In addition, the present invention provides a method of delivering a drug for treating a neurodevelopmental disease, a neurologic disease, or a psychiatric disease, the method comprising administering a composition comprising vesicles derived from *Micrococcus luteus* containing a drug for treating a neurodevelopmental disease, a neurologic disease, or a psychiatric disease to be targeted as an active ingredient to a subject in need thereof.

In addition, the present invention provides a use of a composition comprising vesicles derived from *Micrococcus luteus* as an active ingredient for delivering a drug for treating a neurodevelopmental disease, a neurologic disease, or a psychiatric disease.

Advantageous Effects

The present inventors confirmed that when vesicles derived from *Micrococcus luteus* were orally administered, the vesicles were absorbed into blood vessels and distributed in brain tissue. Further, the present inventors confirmed that when epithelial cells and inflammatory cells were treated with the vesicles, the secretion of inflammatory mediators by pathogenic factors was remarkably suppressed, and when cells were treated with the vesicles, NLRP3 protein expression and NF-kB(p65) signals induced by pathogenic factors were suppressed. In addition, the present inventors confirmed that when cells were treated with the vesicles, eNOS signals suppressed by pathogenic factors were increased. Furthermore, the present inventors confirmed that when neurological cells were treated with the vesicles, the expression of a BDNF gene suppressed by pathogenic factors was restored. Further, the present inventors confirmed that when neurological cells were treated with the vesicles, the expression of sirtuin 1 and sirtuin 7 genes suppressed by pathogenic factors was restored. In addition, the present inventors confirmed that when the vesicles were administered to a neurologic disease mouse model, cognitive function was significantly restored. Furthermore, the present inventors confirmed that when the vesicles were administered to the neurologic disease mouse model, neurogenesis was significantly restored, so that the vesicles derived from *Micrococcus luteus* according to the present invention may be usefully used for the development of a medicine, health functional food, or the like for preventing a neurodevelopmental disease, a neurological disorder, or a psychiatric disease such as Alzheimer's disease, Parkinson's disease, amyotropic lateral sclerosis, Huntington's disease, epilepsy, multiple sclerosis, chronic inflammatory demyelinating polyneuropathy, diabetic neuropathy, autism spectrum disorder, attention deficit hyperactivity syndrome, major depressive disorder, bipolar disorder, anxiety disorders, schizophrenia, obsessive compulsive disorder, post-traumatic stress disorder, dissociative disorders, eating disorders, substance use disorder, and personality disorders, alleviating symptoms thereof, or treating the disorders, and will be able to be usefully used as a drug delivery system for treating the neurodevelopmental disease, the neurologic disease, or the psychiatric disease.

BEST MODE

Figure 1:
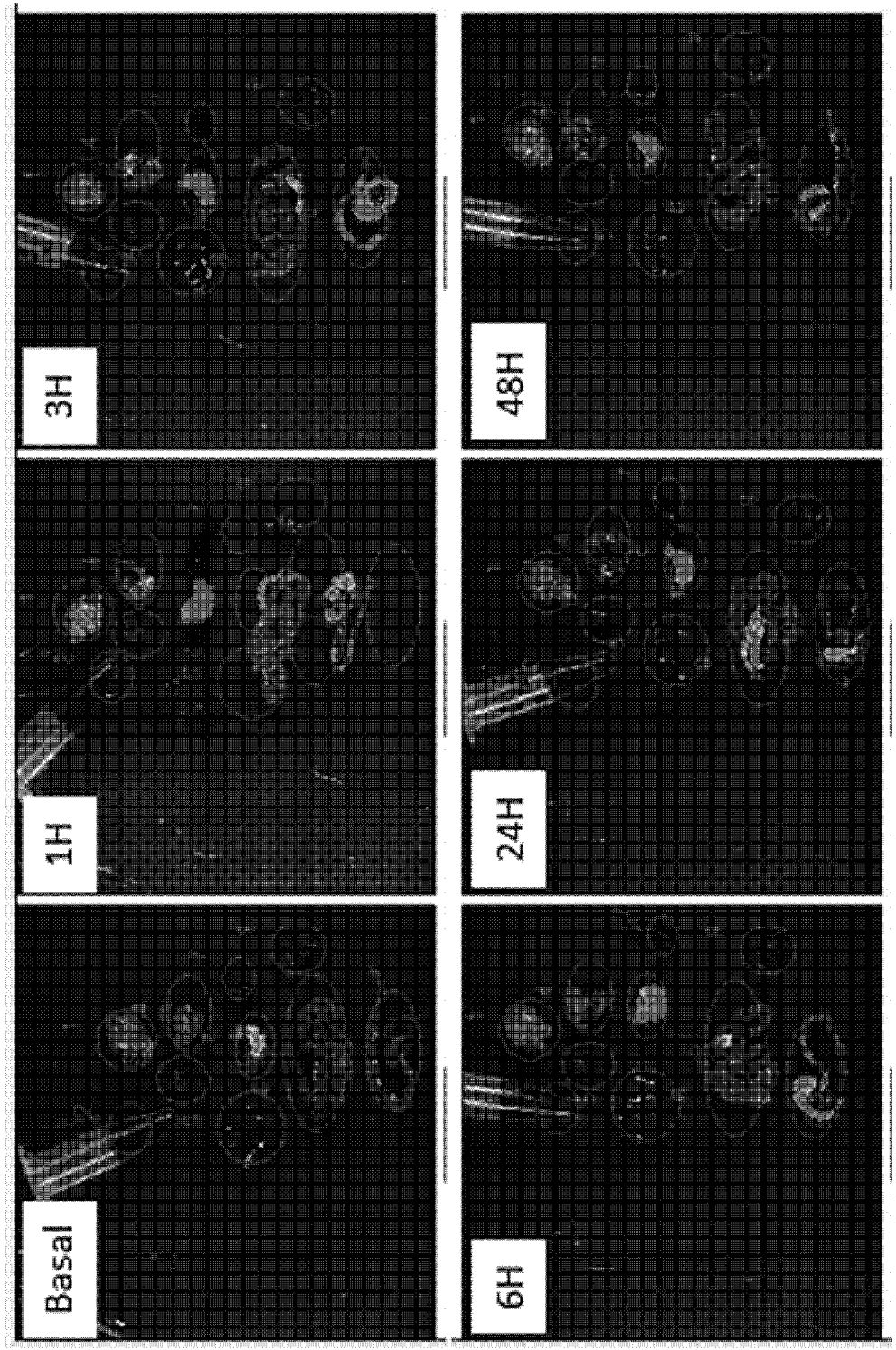
FIG. 1 shows a result of measuring fluorescence intensity in each organ by removing the organ over time after vesicles derived from *Micrococcus luteus* are orally administered to mice.

The present invention relates to vesicles derived from *Micrococcus luteus* and a use thereof.

Hereinafter, the present invention will be described in detail.

The present inventors confirmed that when vesicles derived from *Micrococcus luteus* were orally administered to mice, the vesicles were systemically absorbed into blood vessels and distributed in brain tissue (see Example 2).

Further, the present inventors confirmed that when epithelial cells and macrophages were treated with the vesicles, the secretion of inflammatory mediators IL-8, TNF-α, and IL-6 by inflammatory factors was remarkably suppressed (see Examples 3 and 4).

In addition, the present inventors confirmed that in the etiology of a neurodevelopmental disease, a neurologic disease, and a psychiatric disease, the expression of a NLRP3 protein which is a key signaling element and the secretion of IL-1β caused by a NLRP3 inflammatosome were remarkably suppressed by vesicles derived from *Micrococcus luteus* (see Example 5).

Furthermore, the present inventors confirmed that JNK which is a signal priming NLRP3 inflammasome formation and the NF-kB(p65) signaling pathway were efficiently suppressed by vesicles derived from *Micrococcus luteus* (see Example 6).

Further, the present inventors confirmed that the activation of eNOS which is an important signal for cell homeostasis was suppressed by inflammatory factors, but were restored by vesicles derived from *Micrococcus luteus* (see Example 7).

In addition, the present inventors confirmed that when vesicles derived from *Micrococcus luteus* were orally administered to a brain disease mouse model, cognitive function, learning ability and memory ability were restored to normal levels, and abnormal protein deposition was also suppressed (see Examples 11 to 14).

Furthermore, the present inventors confirmed that in the brain disease mouse model, when vesicles derived from *Micrococcus luteus* were orally administered, the proliferation, migration, and differentiation of neural stem cells were restored to normal levels, and dendrite formation, which is important for inter-neuronal integration, was also restored to a normal level (see Examples 15 and 16).

Further, the present inventors confirmed that when an abnormal protein was administered to nerve cells, the expression of a neurogenesis mediator, the BDNF gene, reduced by the abnormal protein was restored to a normal level, and the expression of sirtuin 1 and sirtuin 7 genes, which are mediators associated with cell homeostasis, was also restored to a normal level (see Examples 9 and 10).

Thus, the present invention provides a pharmaceutical composition for preventing or treating a neurodevelopmental disease, a neurologic disease, or a psychiatric disease, comprising vesicles derived from *Micrococcus luteus* as an active ingredient.

In addition, the present invention may provide an anti-aging pharmaceutical composition, comprising vesicles derived from *Micrococcus luteus* as an active ingredient.

As used herein, the term "extracellular vesicle" or "vesicle" refers to a structure formed of a nano-sized membrane secreted from various bacteria, and includes, for example, a vesicle derived from gram-negative bacteria such as *E. coli*, which has, an endotoxin (lipopolysaccharide), a toxic protein, and both bacterial DNA and RNA, or a vesicle derived from gram-positive bacteria such as bacteria of the genus *Micrococcus*, which have outer membrane vesicles (OMVs), a protein and a nucleic acid as well as components of a bacterial cell wall, such as peptidoglycan and lipoteichoic acid.

In the present invention, the extracellular vesicles or vesicles encompasses all structures which are naturally secreted from *Micrococcus luteus*, or formed of an artificially produced membrane, and in the present invention, the extracellular vesicles or vesicles may be represented by MDH-101, MDH-101 EVs, *M. luteus* EVs or MlEVs.

The vesicles may be isolated by heat treatment or autoclaving during *Micrococcus luteus* culture, or using one or more methods selected from the group consisting of centrifugation, ultracentrifugation, autoclaving, extrusion, sonication, cell lysis, homogenization, freezing-thawing, electroporation, mechanical degradation, chemical treatment, filtration with a filter, gel filtration chromatography, pre-flow electrophoresis, and capillary electrophoresis of the cell culture. In addition, for isolation, washing for removing impurities, and concentration of the obtained vesicles may be further performed.

In the present invention, vesicles isolated by the method are in the form of a sphere, and may have an average diameter 10 to 200 nm, 10 to 190 nm, 10 to 180 nm, 10 to 170 nm, 10 to 160 nm, 10 to 150 nm, 10 to 140 nm, 10 to 130 nm, 10 to 120 nm, 10 to 110 nm, 10 to 100 nm, 10 to 90 nm, 10 to 80 nm, 10 to 70 nm, 10 to 60 nm, 10 to 50 nm, 20 to 200 nm, 20 to 180 nm, 20 to 160 nm, 20 to 140 nm, 20 to 120 nm, 20 to 100 nm, or 20 to 80 nm, preferably 20 to 200 nm, but the average diameter is not limited thereto.

As used herein, the term "comprised as an active ingredient" used herein refers to comprise a sufficient amount for achieving the efficacy or activity of *Micrococcus luteus*-derived vesicles.

As used herein, the term "neurodevelopmental disease" refers to all developmental diseases associated with developmental delay or damage to the central nervous system including the brain, a neurodevelopmental disease is known as a disease caused by developmental diseases of the brain rather than psychosocial problems, and examples thereof may include, for example, intellectual disabilities, communication disorders, autism spectrum disorders, attention deficit hyperactivity disorders, specific learning disorders, motor disorders, and the like.

As used herein, the term "neurologic diseases" refers to a disease caused by abnormalities in the nervous system, that is, the brain, spinal cord, nerves, and the like, and in the present invention, the neurologic disease may be a degenerative neurologic disease or an inflammatory neurologic disease, and any disease or pathological condition caused by damage to nerve cells may be included without limitation.

As used herein, the term "degenerative neurologic disease" refers to a disease that occurs in the brain among degenerative diseases that occur with aging, and examples thereof may include Alzheimer's disease, Parkinson's disease, amyotropic lateral sclerosis, Huntington's disease, epilepsy, Kearns-Sayre syndrome (KSS), chronic progressive external ophthalmoplegia (CPEO), mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), Leigh syndrome (LS), mitochondrial recessive ataxia syndrome, and the like.

As used herein, the term "inflammatory neurologic disease" refers to a disease caused by the influence of neuroinflammation occurring in the central nervous system, and examples thereof may include multiple sclerosis, chronic inflammatory demyelinating polyneuropathy, diabetic neuropathy, and the like.

As used herein, the term "psychiatric disease" refers to a pathological mental state that affects things such as thoughts, feelings, and behaviors of a person, and is a general term for a state in which mental function is impaired, and examples thereof may include major depressive disorder, bipolar disorder, anxiety disorders, schizophrenia, obsessive compulsive disorder, post-traumatic stress disorder, dissociative disorders, eating disorders, substance use disorder, personality disorders, and the like.

As used herein, the term "anxiety disorder" refers to a mental disorder in which a person feels anxiety for no reason or has an excessive degree of anxiety, and examples thereof may include panic disorders, social anxiety disorders, generalized anxiety disorders, specific phobias, and the like.

As used herein, the term "personality disorder" refers to pathological emotions, thoughts, and behavioral modes of an individual, which have begun to develop gradually from an early age and become stronger in adolescents or early adults, and examples thereof may include paranoid personality disorder, antisocial personality disorder, borderline personality disorder, narcissistic personality disorder, avoidant personality disorder, dependent personality disorder, and the like.

In the present invention, the neurodevelopmental disease, neurologic disease, or psychiatric disease may be a disease caused by neurogenesis dysfunction, and more specifically, may be a disease caused by mitochondrial dysfunction due to various stresses, or neurogenesis dysfunction due to nerve cell damage, neuroinflammation, and/or neurodegeneration mediated by a NLRP3 inflammasome.

The "neurogenesis" refers to a process in which nerve cells are generated from neural stem cells, and may include adult neurogenesis.

As used herein, the term "mediated by a NLR family pyrin domain containing 3 inflammasome (NLRP3 inflammasome)" means being generated by nerve damage caused by excessive NLRP3 inflammasome formation inducing a neuroinflammation response via various signaling pathways, and according to an example of the present invention, since the *Micrococcus luteus*-derived vesicles may suppress NLRP3 inflammasome formation by suppressing a signaling pathway priming NLRP3 inflammasome formation, a neurodevelopmental disease, neurologic disease, or psychiatric disease mediated by the NLR family pyrin domain containing 3 inflammasome (NLRP3 inflammasome) may be effectively prevented, alleviated, or treated by the suppression of the NLRP3 inflammasome formation.

As used herein, the term "anti-aging" refers to delaying aging as much as possible by preventing and suppressing aging, and according to an example of the present invention, a composition comprising the vesicle as an active ingredient may suppress the aging of the brain or nerve cells by suppressing neurogenesis dysfunction.

The amount of the vesicles in the composition of the present invention may be appropriately adjusted depending on the symptoms of a disease, the degree of progression of symptoms, the condition of a patient, and the like, and may range from, for example, 0.0001 wt % to 99.9 wt % or 0.001 wt % to 50 wt % with respect to a total weight of the composition, but the present invention is not limited thereto. The amount ratio is a value based on the amount of dried product from which a solvent is removed.

The pharmaceutical composition according to the present invention may further include a suitable carrier, excipient, and diluent which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled release additive.

The pharmaceutical composition according to the present invention may be used by being formulated, according to commonly used methods, into a form such as powders, granules, sustained-release-type granules, enteric granules, liquids, eye drops, elixirs, emulsions, suspensions, spirits, troches, aromatic water, lemonades, tablets, sustained-release-type tablets, enteric tablets, sublingual tablets, hard capsules, soft capsules, sustained-release-type capsules, enteric capsules, pills, tinctures, soft extracts, dry extracts, fluid extracts, injections, capsules, perfusates, or a preparation for external use, such as plasters, lotions, pastes, sprays, inhalants, patches, sterile injectable solutions, or aerosols. The preparation for external use may have a formulation such as creams, gels, patches, sprays, ointments, plasters, lotions, liniments, pastes, or cataplasmas.

As the carrier, the excipient, and the diluent that may be included in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

For formulation, commonly used diluents or excipients such as fillers, thickeners, binders, wetting agents, disintegrants, and surfactants are used.

As additives of tablets, powders, granules, capsules, pills, and troches according to the present invention, excipients such as corn starch, potato starch, wheat starch, lactose, white sugar, glucose, fructose, D-mannitol, precipitated calcium carbonate, synthetic aluminum silicate, dibasic calcium phosphate, calcium sulfate, sodium chloride, sodium hydrogen carbonate, purified lanolin, microcrystalline cellulose, dextrin, sodium alginate, methyl cellulose, sodium carboxymethylcellulose, kaolin, urea, colloidal silica gel, hydroxypropyl starch, hydroxypropyl methylcellulose (HPMC) 1928, HPMC 2208, HPMC 2906, HPMC 2910, propylene glycol, casein, calcium lactate, and Primojel®; and binders such as gelatin, Arabic gum, ethanol, agar powder, cellulose acetate phthalate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch, hydroxypropyl cellulose, hydroxypropyl methylcellulose, polyvinyl alcohol, and polyvinylpyrrolidone may be used, and disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxypropylcellulose, dextran, ion-exchange resin, polyvinyl acetate, formaldehyde-treated casein and gelatin, alginic acid, amylose, guar gum, sodium bicarbonate, polyvinylpyrrolidone, calcium phosphate, gelled starch, Arabic gum, amylopectin, pectin, sodium polyphosphate, ethyl cellulose, white sugar, magnesium aluminum silicate, a di-sorbitol solution, and light anhydrous silicic acid; and lubricants such as calcium stearate, magnesium stearate, stearic acid, hydrogenated vegetable oil, talc, lycopodium powder, kaolin, Vaseline, sodium stearate, cacao butter, sodium salicylate, magnesium salicylate, polyethylene glycol 4000, PEG 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid may be used.

As additives of liquids according to the present invention, water, dilute hydrochloric acid, dilute sulfuric acid, sodium citrate, monostearic acid sucrose, polyoxyethylene sorbitol fatty acid esters (twin esters), polyoxyethylene monoalkyl ethers, lanolin ethers, lanolin esters, acetic acid, hydrochloric acid, ammonia water, ammonium carbonate, potassium hydroxide, sodium hydroxide, prolamine, polyvinylpyrrolidone, ethylcellulose, and sodium carboxymethylcellulose may be used.

In syrups according to the present invention, a white sugar solution, other sugars or sweeteners, and the like may be used, and as necessary, a fragrance, a colorant, a preservative, a stabilizer, a suspending agent, an emulsifier, a viscous agent, or the like may be used.

In emulsions according to the present invention, purified water may be used, and as necessary, an emulsifier, a preservative, a stabilizer, a fragrance, or the like may be used.

In suspensions according to the present invention, suspending agents such as acacia, tragacanth, methylcellulose, carboxymethylcellulose, sodium carboxymethylcellulose, microcrystalline cellulose, sodium alginate, hydroxypropyl methylcellulose (HPMC) 1828, HPMC 2906, HPMC 2910, and the like may be used, and as necessary, a surfactant, a preservative, a stabilizer, a colorant, and a fragrance may be used.

Injections according to the present invention may include: solvents such as distilled water for injection, a 0.9% sodium chloride solution, Ringer's solution, a dextrose solution, a dextrose+sodium chloride solution, PEG, lactated Ringer's solution, ethanol, propylene glycol, non-volatile oil-sesame oil, cottonseed oil, peanut oil, soybean oil, corn oil, ethyl oleate, isopropyl myristate, and benzene benzoate; cosolvents such as sodium benzoate, sodium salicylate, sodium acetate, urea, urethane, monoethylacetamide, butazolidine, propylene glycol, the Tween series, amide nicotinate, hexamine, and dimethylacetamide; buffers such as weak acids and salts thereof (acetic acid and sodium acetate), weak bases and salts thereof (ammonia and ammonium acetate), organic compounds, proteins, albumin, peptone, and gums; isotonic agents such as sodium chloride; stabilizers such as sodium bisulfite ($NaHSO_3$) carbon dioxide gas, sodium metabisulfite ($Na_2S_2O_5$), sodium sulfite ($Na_2SO_3$), nitrogen gas ($N_2$), and ethylenediamine tetraacetic acid; sulfating agents such as 0.1% sodium bisulfide, sodium formaldehyde sulfoxylate, thiourea, disodium ethylenediaminetetraacetate, and acetone sodium bisulfite; a pain relief agent such as benzyl alcohol, chlorobutanol, procaine hydrochloride, glucose, and calcium gluconate; and suspending agents such as sodium CMC, sodium alginate, Tween 80, and aluminum monostearate.

In suppositories according to the present invention, bases such as cacao butter, lanolin, Witepsol, polyethylene glycol, glycerogelatin, methylcellulose, carboxymethylcellulose, a mixture of stearic acid and oleic acid, Subanal, cottonseed oil, peanut oil, palm oil, cacao butter+cholesterol, lecithin, lanette wax, glycerol monostearate, Tween or span, imhausen, monolan(propylene glycol monostearate), glycerin, Adeps solidus, buytyrum Tego-G, cebes Pharma 16, hexalide base 95, cotomar, Hydrokote SP, S-70-XXA, S-70-XX75(S-70-XX95), Hydrokote 25, Hydrokote 711, idropostal, massa estrarium (A, AS, B, C, D, E, I, T), masa-MF, masupol, masupol-15, neosuppostal-N, paramount-B, supposiro OSI, OSIX, A, B, C, D, H, L, suppository base IV types AB, B, A, BC, BBG, E, BGF, C, D, 299, suppostal N, Es, Wecoby W, R, S, M, Fs, and tegester triglyceride matter (TG-95, MA, 57) may be used.

Solid preparations for oral administration include tablets, pills, powders, granules, capsules, and the like, and such solid preparations are formulated by mixing the composition with at least one excipient, e.g., starch, calcium carbonate, sucrose, lactose, gelatin, and the like. In addition to simple excipients, lubricants such as magnesium stearate and talc are also used.

Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a fragrance, a preservative, and the like. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate.

The pharmaceutical composition according to the present invention is administered in a pharmaceutically effective amount. In the present invention, "the pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

The pharmaceutical composition of the present invention may be administered to an individual via various routes. All administration methods can be predicted, and the pharmaceutical composition may be administered via, for example, oral administration, subcutaneous injection, intraperitoneal administration, intravenous injection, intramuscular injection, intrathecal (space around the spinal cord) injection, sublingual administration, administration via the buccal mucosa, intrarectal insertion, intravaginal insertion, ocular administration, intra-aural administration, intranasal administration, inhalation, spraying via the mouth or nose, transdermal administration, percutaneous administration, or the like.

The pharmaceutical composition of the present invention is determined depending on the type of a drug, which is an active ingredient, along with various related factors such as a disease to be treated, administration route, the age, gender, and body weight of a patient, and the severity of diseases. Specifically, the effective amount of the composition according to the present invention may vary depending on the patient's age, sex, and body weight, and generally, 0.001 to 150 mg of the composition and preferably, 0.01 to 100 mg of the composition, per 1 kg of the body weight, may be administered daily or every other day or may be administered once to three times a day. However, since the effective amount may be increased or decreased depending on the administration route, the severity of obesity, gender, body weight, age, and the like, the dosage is not intended to limit the scope of the present invention in any way.

In addition, the present invention provides a method for preventing or treating a neurodevelopmental disease, a neurologic disease, or a psychiatric disease, the method comprising administering a composition comprising vesicles derived from *Micrococcus luteus* as an active ingredient to a subject in need thereof.

In addition, the present invention provides a use of a composition comprising vesicles derived from *Micrococcus luteus* as an active ingredient for preventing or treating a neurodevelopmental disease, a neurologic disease, or a psychiatric disease.

In addition, the present invention provides a use of vesicles derived from *Micrococcus luteus* for preparing a drug for treating a neurodevelopmental disease, a neurologic disease, or a psychiatric disease.

As used herein, the "subject" refers to a subject in need of treatment of a disease, and more specifically, refers to a mammal such as a human or a non-human primate, a mouse, a rat, a dog, a cat, a horse, and a cow, but the present invention is not limited thereto.

As used herein, the "administration" refers to providing a subject with a predetermined composition of the present invention by using an arbitrary appropriate method.

The term "prevention" as used herein means all actions that inhibit or delay the onset of a target disease. The term "treatment" as used herein means all actions that alleviate or beneficially change a target disease and abnormal metabolic symptoms caused thereby via administration of the pharmaceutical composition according to the present invention. The term "improvement" as used herein means all actions that reduce the degree of parameters related to a target disease, e.g., symptoms via administration of the composition according to the present invention.

In addition, the present invention provides a food composition for preventing or alleviating a neurodevelopmental disease, a neurologic disease, or a psychiatric disease, comprising vesicles derived from *Micrococcus luteus* as an active ingredient.

In addition, the present invention may provide an anti-aging food composition, comprising vesicles derived from *Micrococcus luteus* as an active ingredient.

The food composition may be a health functional food composition, but is not limited thereto.

The vesicles according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range, and the vesicles have no problem in terms of stability, so the active ingredient may be used in an amount more than the above-mentioned range.

The type of food is not particularly limited. Examples of food to which the material may be added include meats, sausage, bread, chocolate, candies, snacks, confectioneries, pizza, instant noodles, other noodles, gums, dairy products including ice creams, various soups, beverages, tea, drinks, alcoholic beverages, vitamin complexes, and the like, and include all health functional foods in a typical sense.

The health beverage composition according to the present invention may contain various flavors or natural carbohydrates, and the like as additional ingredients as in a typical beverage. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As a sweetener, it is possible to use a natural sweetener such as thaumatin and *stevia* extract, a synthetic sweetener such as saccharin and aspartame, and the like. The proportion of the natural carbohydrates is generally about 0.01 to 0.20 g, or about 0.04 to 0.10 g per 100 ml of the composition of the present invention.

In addition to the aforementioned ingredients, the composition of the present invention may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

In addition, the present invention provides an inhalant composition for preventing or treating a neurodevelopmental disease, a neurologic disease, or a psychiatric disease, comprising vesicles derived from *Micrococcus luteus* as an active ingredient.

In the case of an inhalant composition, the compound may be formulated according to a method known in the art, and may be conveniently delivered in the form of an aerosol spray from a pressurized pack or a nebulizer by using a suitable propellant, for example, dichlorofluoromethane, trichlorofluoromethane, dichlorotetrafluoroethane, carbon dioxide, or other suitable gases. In the case of the pressurized aerosol, a dosage unit may be determined by providing a valve for transferring a metered amount. For example, a gelatin capsule and a cartridge for use in an inhaler or insufflator may be formulated so as to contain a powder mixture of a compound and a suitable powder base such as lactose or starch.

In addition, the present invention provides a composition for delivering a drug for treating a neurodevelopmental disease, a neurologic disease, or a psychiatric disease, comprising vesicles derived from *Micrococcus luteus* as an active ingredient.

As used herein, the term "drug delivery" refers to all means or actions which load and deliver a drug such as a protein, an antibody, a polymer compound, a low-molecular weight compound, siRNA, and an oligonucleotide to the vesicle according to the present invention in order to deliver the drug to a specific organ, tissue, cell, or organelle.

In the present invention, the composition for delivering a drug may deliver the drug to one or more organs selected from the group consisting of the stomach, small intestine, large intestine, lungs, liver, kidneys, and brain, and preferably may deliver the drug to the brain, but is not limited thereto.

Further, the present invention provides a method of delivering a drug for treating a neurodevelopmental disease, a neurologic disease, or a psychiatric disease, the method comprising administering a composition comprising vesicles derived from *Micrococcus luteus* containing a drug for treating a neurodevelopmental disease, a neurologic disease, or a psychiatric disease to be targeted as an active ingredient to a subject in need thereof.

In addition, the present invention provides a use of a composition comprising vesicles derived from *Micrococcus luteus* as an active ingredient for delivering a drug for treating a neurodevelopmental disease, a neurologic disease, or a psychiatric disease.

In addition, the present invention provides a pharmaceutical composition for preventing or treating a neurodevelopmental disease, a neurologic disease, or a psychiatric disease, comprising vesicles derived from bacteria of the genus *Micrococcus* as an active ingredient.

Modes of the Invention

Hereinafter, preferred Examples for helping the understanding of the present invention will be suggested. However, the following Examples are provided only to more easily understand the present invention, and the contents of the present invention are not limited by the following Examples.

EXAMPLES

Example 1. Isolation of Vesicles from *Micrococcus luteus* Culture Fluid

After culturing a *Micrococcus luteus* strain, vesicles thereof were isolated, analyzed and characterized. *Micrococcus luteus* was cultured in a de Man-Rogosa and Sharpe (MRS) medium until absorbance (OD 600) became 1.0 to 1.5 in a 37° C. aerobic chamber, and then sub-cultured. Subsequently, the medium supernatant containing the strain was recovered, centrifuged at 10,000 g and 4° C. for 20 minutes, and the strain was removed and then filtered through a 0.22-μm filter. And the filtered supernatant was concentrated to a volume of 50 mL using a 100 kDa Pellicon 2 Cassette filter membrane (Merck Millipore, US) and a MasterFlex pump system (Cole-Parmer, US) through microfiltration. Then, the concentrated supernatant was filtered again using a 0.22 μm filter. Subsequently, the protein was quantified using a BCA assay, and the following experiments were performed on the obtained vesicles.

Example 2. Evaluation of Pharmacokinetic Characteristics of Vesicles Derived from *Micrococcus luteus*

In order to investigate the pharmacokinetic characteristics of vesicles derived from *Micrococcus luteus* during oral administration, the fluorescence expressed in the body and each organ from immediately before administration to 48 hours after administration was measured by orally administering vesicles derived from *Micrococcus luteus* stained with a fluorescent staining reagent to mice.

Figure 2:
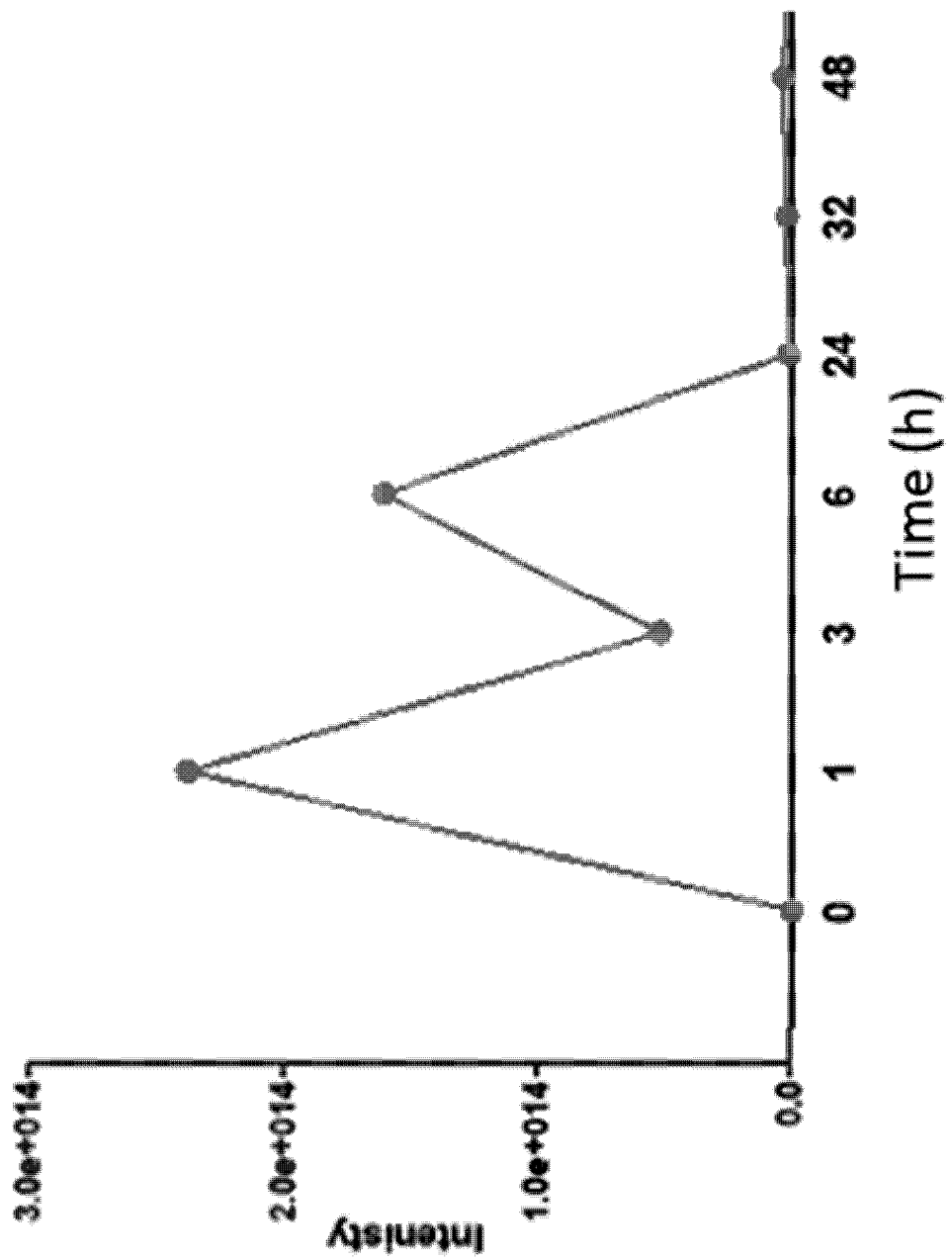
FIG. 2 is a view illustrating the pattern in which vesicles are distributed in brain tissue over time after vesicles derived from *Micrococcus luteus* are orally administered to mice.

As shown in FIG. 1, when long-term distribution over time of fluorescence-stained vesicles derived from *Micrococcus luteus* was confirmed with an image, it can be confirmed that the vesicles were distributed in several organs. Further, as illustrated in FIG. 2, it could be confirmed that the vesicles were distributed in brain tissue within 1 hour after oral administration, and continuously distributed in brain tissue up to 24 hours.

Figure 3:
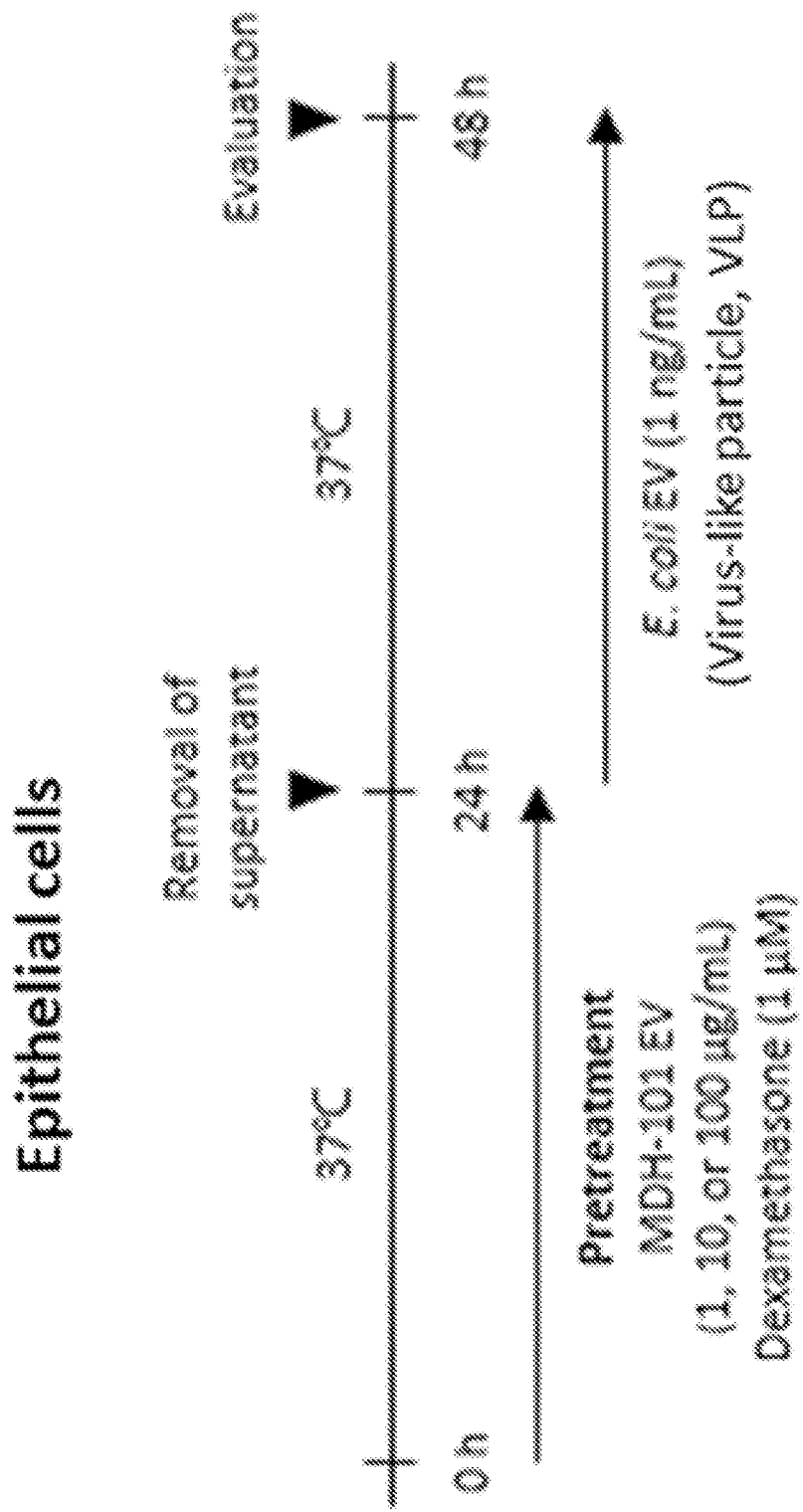
FIG. 3 is a view illustrating an experimental protocol for evaluating the effect of suppressing the secretion of an inflammatory mediator by an *E. coli*-derived vesicle (*E. coli* EV), which is an inflammatory causative factor by administering a vesicle (MDH-101 EV) derived from *Micrococcus luteus* or a positive control drug dexamethasone (Dex) to epithelial cells.

Example 3. Evaluation of Anti-Inflammatory Effect of Vesicles Derived from *Micrococcus luteus* in Epithelial Cells As shown in FIG. 3, epithelial cells were pre-treated with vesicles derived from *Micrococcus luteus* (MDH-101 EV) and a positive control drug, dexamethasone, and after treatment with vesicles derived from *E. coli* (*E. coli* EVs) inducing inflammation, a secretion level of an inflammatory cytokine such as IL-8 was measured using enzyme-linked immunosorbent assay (ELISA, R&D Systems). Specifically, epithelial cells were pre-treated with vesicles derived from *Micrococcus luteus* at various concentrations (1, 10 and 100 µg/mL) for 24 hours, and then treated with vesicles derived from *E. coli* at a concentration of 1 ng/mL for 24 hours, followed by measuring IL-8 secreted into the medium.

Figure 4A:
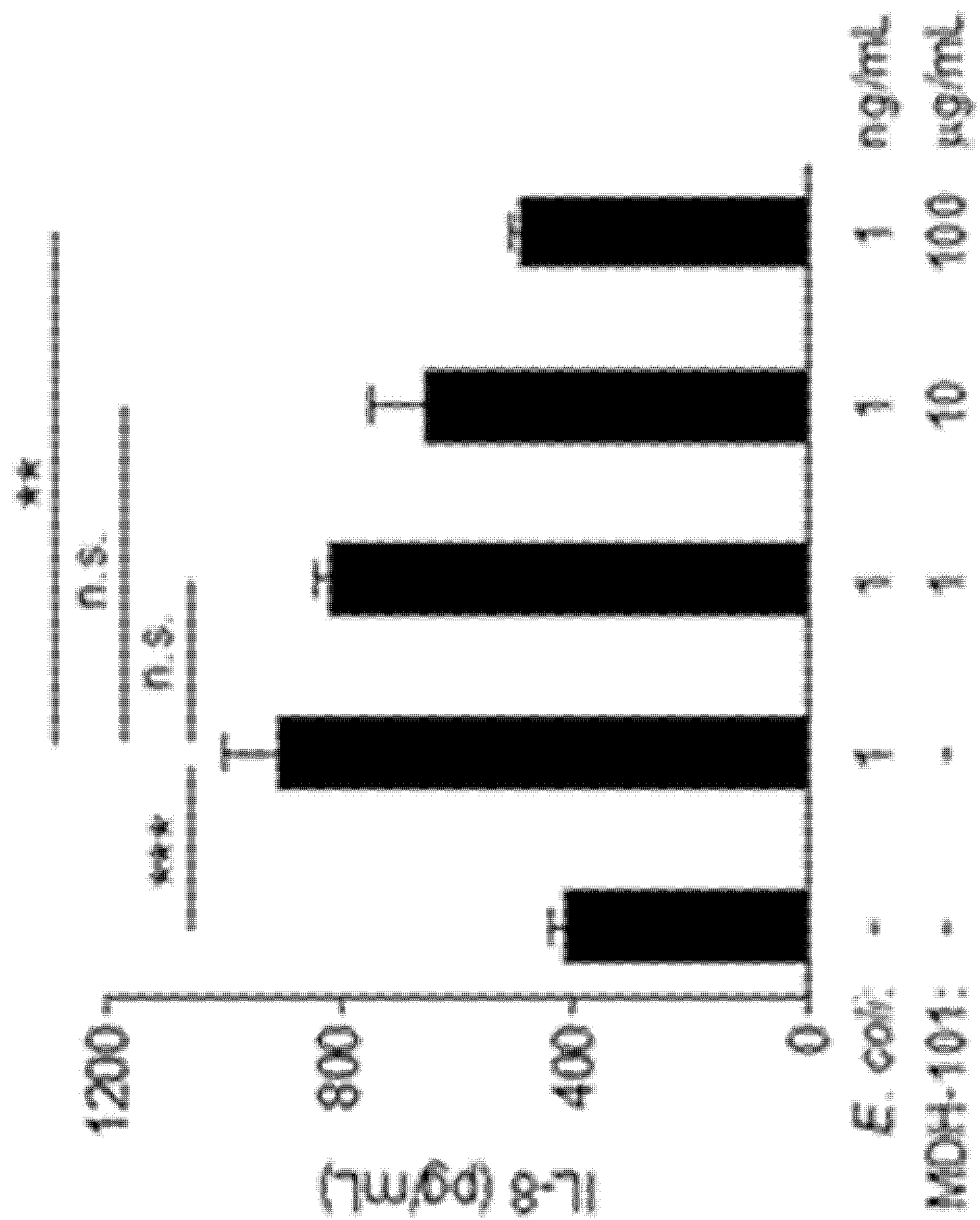
FIGS. 4A and 4B are views illustrating the dose dependence (A) of vesicles derived from *Micrococcus luteus* for suppressing the secretion of an inflammatory mediator IL-8 by an *E. coli*-derived vesicle (*E. coli*) and experimental results (B) comparing the efficacy with a control drug dexamethasone, by administering a vesicle (MDH-101) derived from *Micrococcus luteus* to epithelial cells.
Figure 4B:
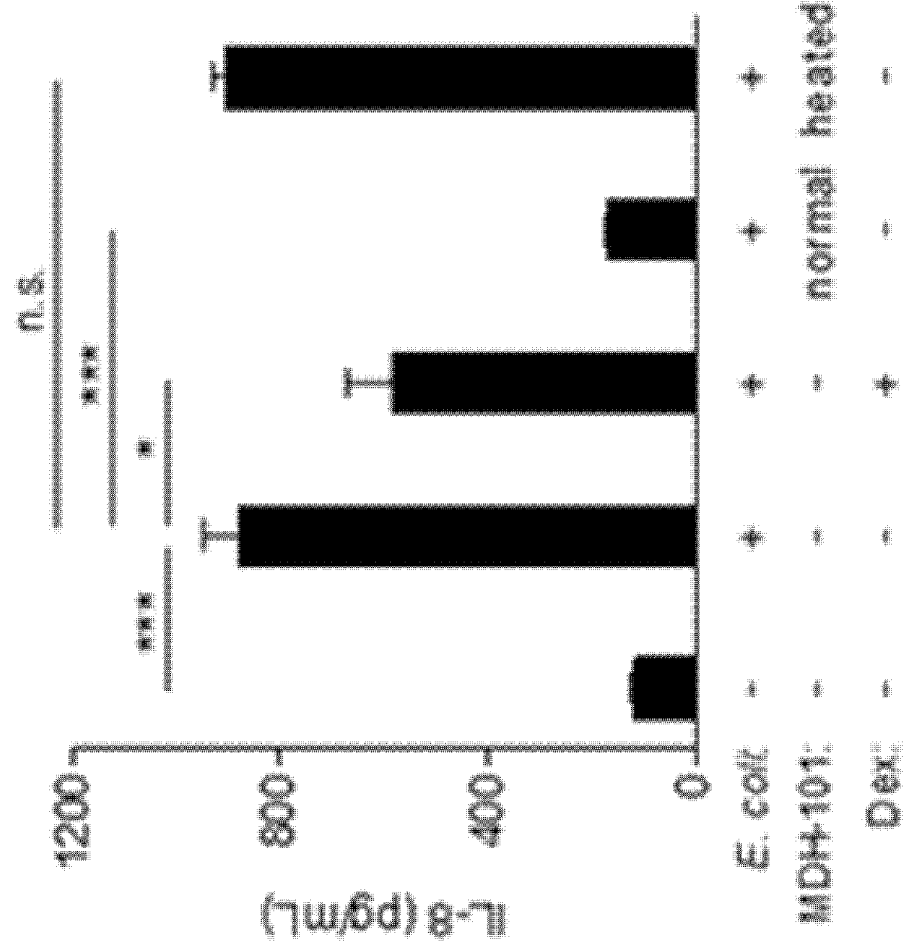

As a result, as shown in FIG. 4A, it was confirmed that IL-8 secretion was inhibited by the vesicles derived from *Micrococcus luteus* in a dose-dependent manner. In addition, as illustrated in FIG. 4B, it was confirmed that when compared to a control drug dexamethasone, the effect of suppressing the secretion of IL-8 of the vesicle was better than the control drug, and when vesicle was heat-treated, the effect of suppressing the secretion of IL-8 disappeared. From the above result, it can be seen that, compared to the representative anti-inflammatory drug, dexamethasone, the vesicles derived from *Micrococcus luteus* have a more excellent anti-inflammatory effect, the anti-inflammatory effect mediated by the vesicles derived from *Micrococcus luteus* disappeared after heat treatment, indicating that the anti-inflammatory action is mediated by a protein in the extracellular vesicles.

Figure 5:
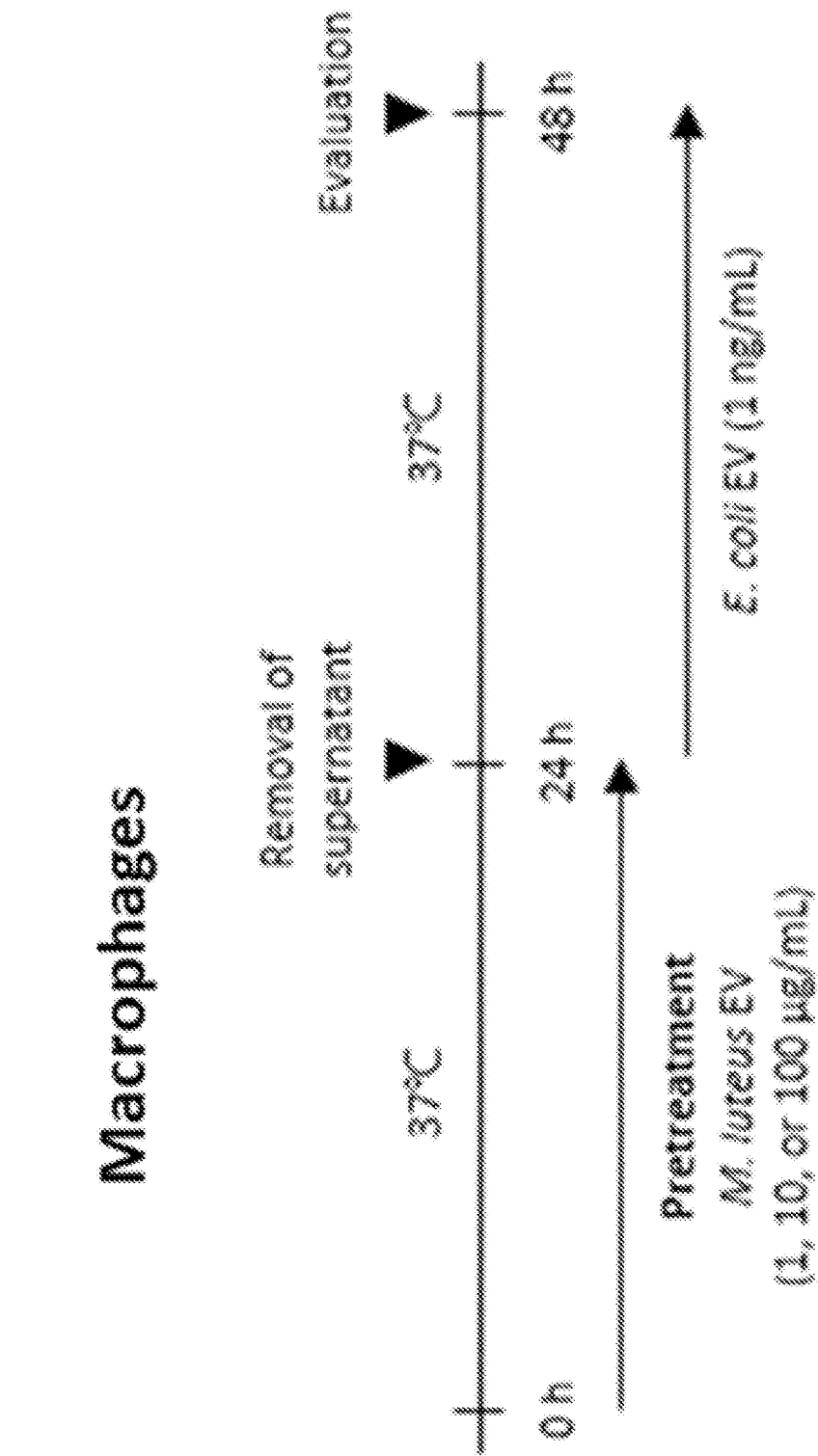
FIG. 5 is a view illustrating an experimental protocol for evaluating the effect of suppressing the secretion of an inflammatory mediator by an *E. coli*-derived vesicle (*E. coli* EV), which is an inflammatory causative factor by administering a vesicle (*M. luteus* EV) derived from *Micrococcus luteus* to macrophages which are inflammatory cells.

Example 4. Evaluation of Anti-Inflammatory Effect of Vesicles Derived from *Micrococcus luteus* in Inflammatory Cells As shown in FIG. 5, macrophages (RAW 264.7 cells) were pre-treated with vesicles derived from *Micrococcus luteus* (*M. luteus* EVs), and then treated with vesicles derived from *E. coli* (*E. coli* EVs) inducing inflammation, followed by measuring levels of inflammatory cytokines, such as TNF-α and IL-6, through ELISA (R&D Systems). Specifically, after macrophages were pre-treated with the vesicles derived from *Micrococcus luteus* at various concentrations (1, 10, and 100 µg/mL) for 24 hours, the secretion amounts of TNF-α and IL-6 secreted to the media were measured by treating the macrophages with an *E. coli*-derived vesicle at a concentration of 1 ng/mL for 24 hours.

Figure 6A:
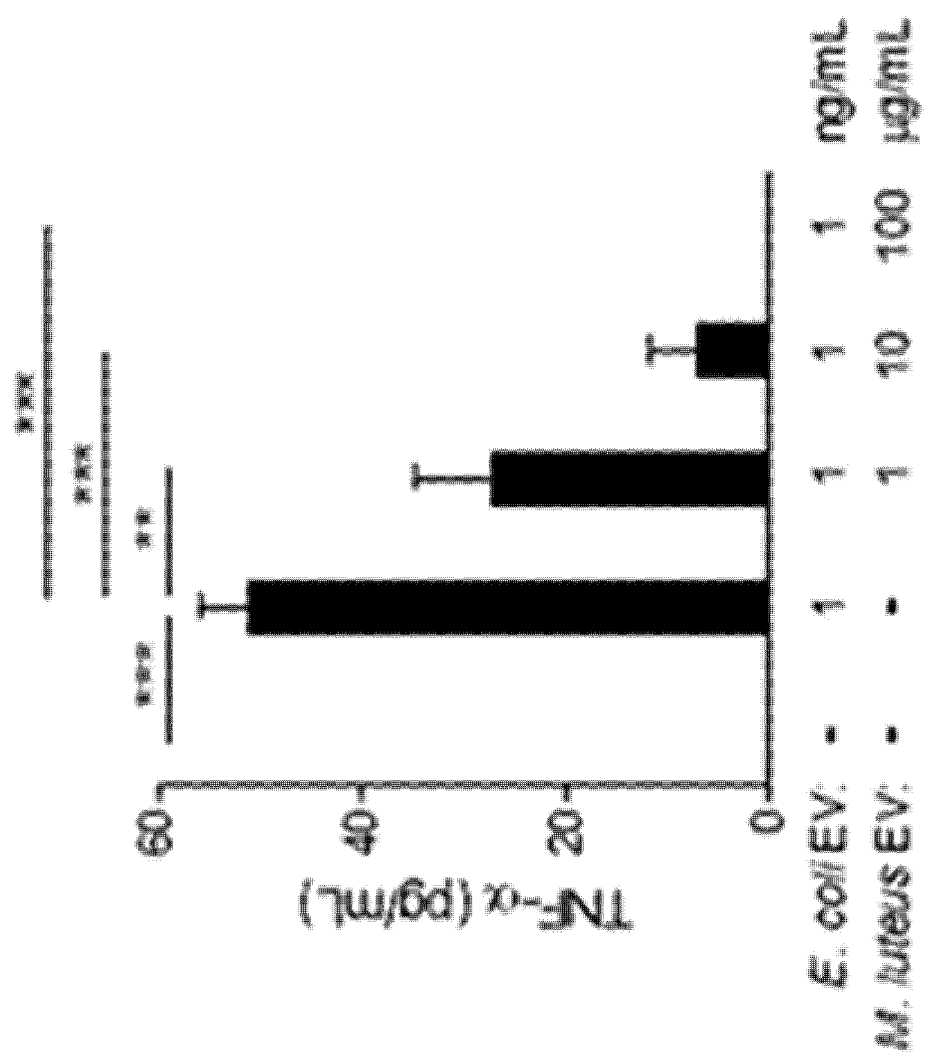
FIGS. 6A and 6B are views illustrating the results of confirming the secretion suppressing effect on inflammatory mediators TNF-α (A) and IL-6 (B) by means of an *E. coli*-derived vesicle (*E. coli* EV) by administering a vesicle (*M. luteus* EV) derived from *Micrococcus luteus* to macrophages.
Figure 6B:
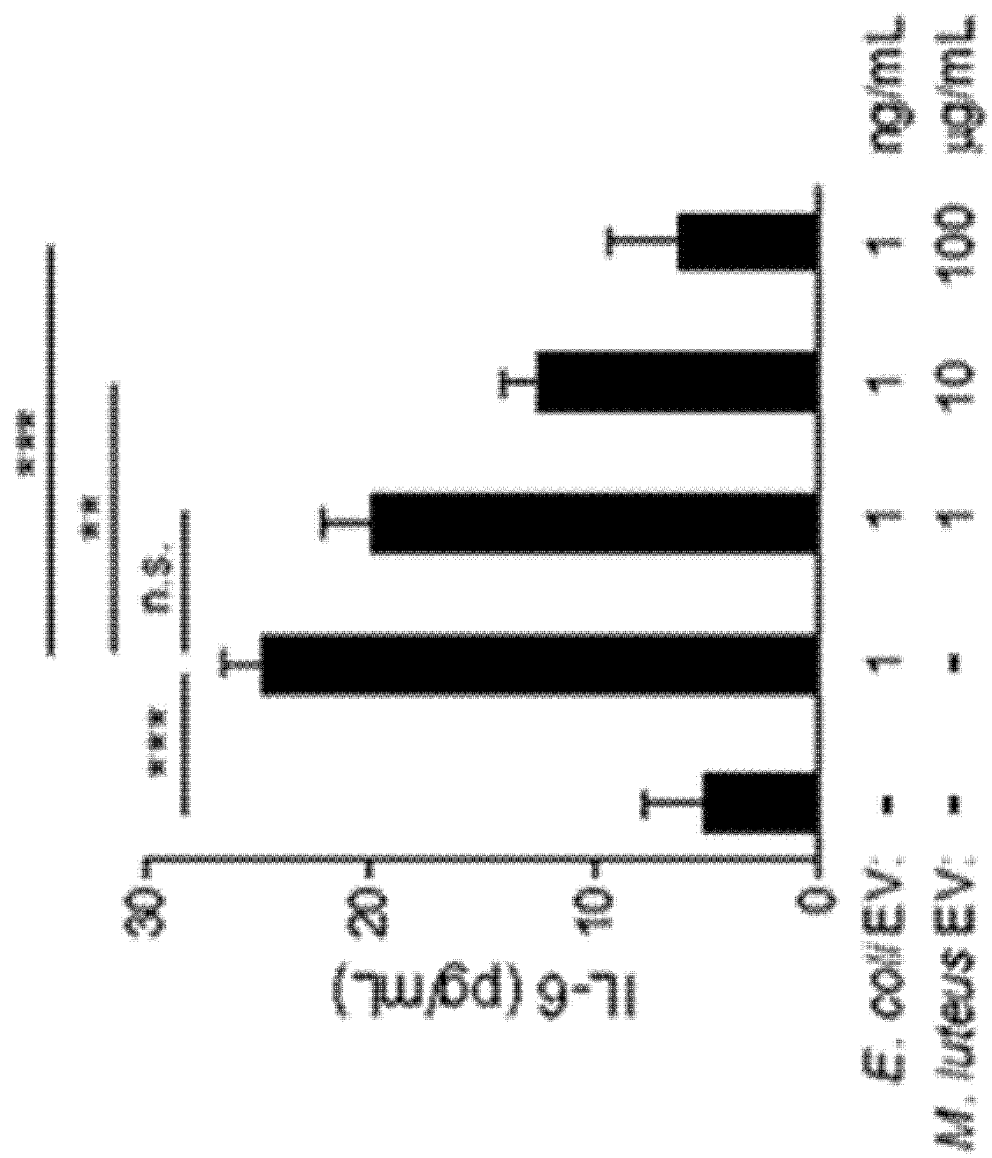

As a result, as illustrated in FIGS. 6A and 6B, it was confirmed that when macrophages were pre-treated with the vesicles derived from *Micrococcus luteus*, the secretion of TNF-α (FIG. 6A) and IL-6 (FIG. 6B) by the *E. coli*-derived vesicle, which is an inflammatory causative factor was suppressed in a dose-dependent manner of the vesicles derived from *Micrococcus luteus*. This means that in inflammatory cells inducing inflammation in a neurodevelopmental disease, neurologic disease, or psychiatric disease, the vesicles derived from *Micrococcus luteus* efficiently suppress the secretion of inflammatory mediators by inflammatory causative factors.

Example 5. Immune Function-Regulating Effect of Vesicles Derived from *Micrococcus luteus* on Immune Dysfunction Caused by Inflammatory Causative Factors It is known that the immune response to various stresses is very important in the pathogenesis of a neurologic disease, or a psychiatric disease. Particularly, an NLRP3 protein present in the cytoplasm is known as a critical signaling pathway in the pathogenesis of a neurodevelopmental disease, a neurologic disease, or a psychiatric disease. In order to evaluate the effect of regulating immune function by the vesicles derived from *Micrococcus luteus*, the expression of NLR family pyrin domain containing 3 (NLRP3), t-box protein expressed in T cells (t-bet), and retineic-acid-receptor-related orphan nuclear receptor gamma (ROR-γt) was confirmed in tissue by western blotting by administering lipopolysaccharide (LPS), which is a representative causative factor inducing immune dysfunction in mice. To measure an expression level of each protein, 50 µg of the protein was used, and in lung tissue of a mouse group to which dexamethasone (Dex) or vesicles derived from *Micrococcus luteus* were administered, protein expression was confirmed.

Figure 7:
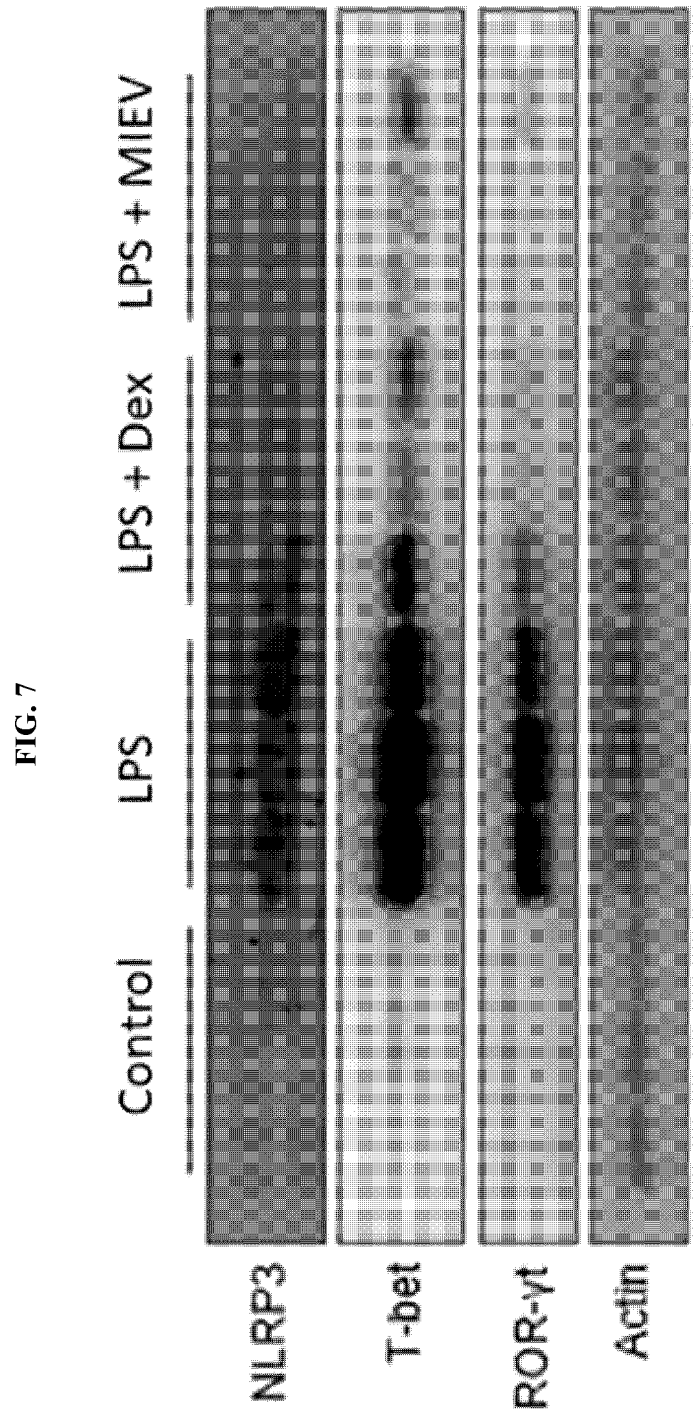
FIG. 7 is a view illustrating the results of confirming the expression patterns of immune function-regulatory proteins NLRP3, T-bet, and ROR-γt in tissues isolated from mice administered lipopolysaccharide (LPS), which is an inflammatory causative factor, in order to evaluate the effect of regulating immune function by a vesicle (MlEV) derived from *Micrococcus luteus*.

As a result, as illustrated in FIG. 7, it was confirmed that in a group (LPS) administered LPS, the expression of the NLRP3 protein was remarkably increased compared to that of the negative control, and in tissue of a group (LPS+MIEV) in which the vesicles derived from *Micrococcus luteus* were administered to the mice administered LPS, the expression of the NLRP3 protein was remarkably suppressed similarly to a group (LPS+Dex) administered dexamethasone. Further, in the group (LPS) administered LPS, the expression of t-bet and ROR-γt proteins was remarkably increased compared to the negative control, and in the group (LPS+MIEV) administered the vesicles derived from *Micrococcus luteus*, the expression of t-bet and ROR-γt proteins was suppressed compared to the group (LPS+Dex) administered dexamethasone. This means that the vesicles derived from *Micrococcus luteus* efficiently suppress innate immune dysfunction by an inflammatory causative factor.

Figure 8:
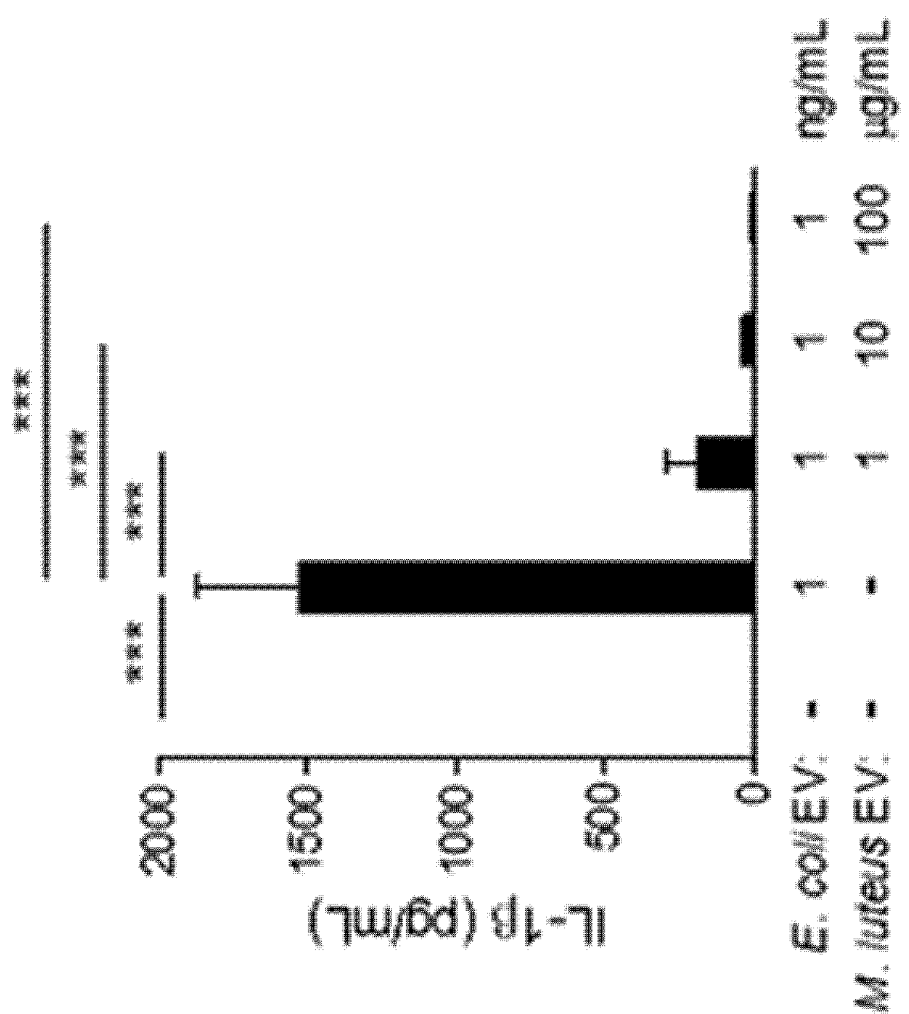
FIG. 8 is a view illustrating the results of confirming the secretion suppressing effect on inflammatory mediators IL-1β by LPS by administering a vesicle (*M. luteus* EV) derived from *Micrococcus luteus* to macrophages.

Further, after macrophages were pre-treated with the vesicles derived from *Micrococcus luteus* by the method in Example 4, the efficacy on the secretion of IL-1β was evaluated by treating the macrophages with LPS. As illustrated in FIG. 8, it was confirmed that in the case of the pre-treatment with the vesicle, the secretion of IL-1β by an inflammatory factor LPS was suppressed in a dose-dependent manner by the vesicle (*M. luteus* EV) derived from *Micrococcus luteus*. This means that in inflammatory cells inducing inflammation in a neurodevelopmental disease, neurologic disease, or psychiatric disease, the vesicles derived from *Micrococcus luteus* efficiently suppress the secretion of IL-1<, which is an inflammatory mediator secreted by the NLRP3 inflammasome.

Example 6. Regulatory Effect of Vesicles Derived from *Micrococcus luteus* on Innate Immune Dysfunction by Inflammatory Factors It is known that the innate immune dysfunction to various stresses is very important in the pathogenesis of a neurologic disease, or a psychiatric disease. It has recently been revealed that in the etiology of an immune disease, the acquired immune response of Th1 and Th17 to specific antigens is a key to immune dysfunction, whereas in the etiology of a neurodevelopmental disease, neurologic disease or psychiatric disease, a NLRP3 inflammasome is formed by various risk factors (danger signals) inducing innate immunity, thereby causing a disease. In addition, in order for risk factors to form the NLP3 inflammasome, a priming process in which the expression of the NLPR3 protein is induced by inflammatory factors such as LPS and TNF-α is important.

In order to evaluate the efficacy of the vesicles derived from *Micrococcus luteus* in the NLRP3 priming process essential for NLRP3 inflammasome formation, the degree of activation of JNK and NF-kB (p65), which are signals associated with innate immune function, was evaluated by western blotting by removing tissues from mice administered LPS by the method in Example 5. 50 µg of protein was used to measure the expression amount of each protein, and the protein expression was evaluated in the tissues of a mouse group administered dexamethasone (Dex) or the vesicles derived from *Micrococcus luteus*.

Figure 9:
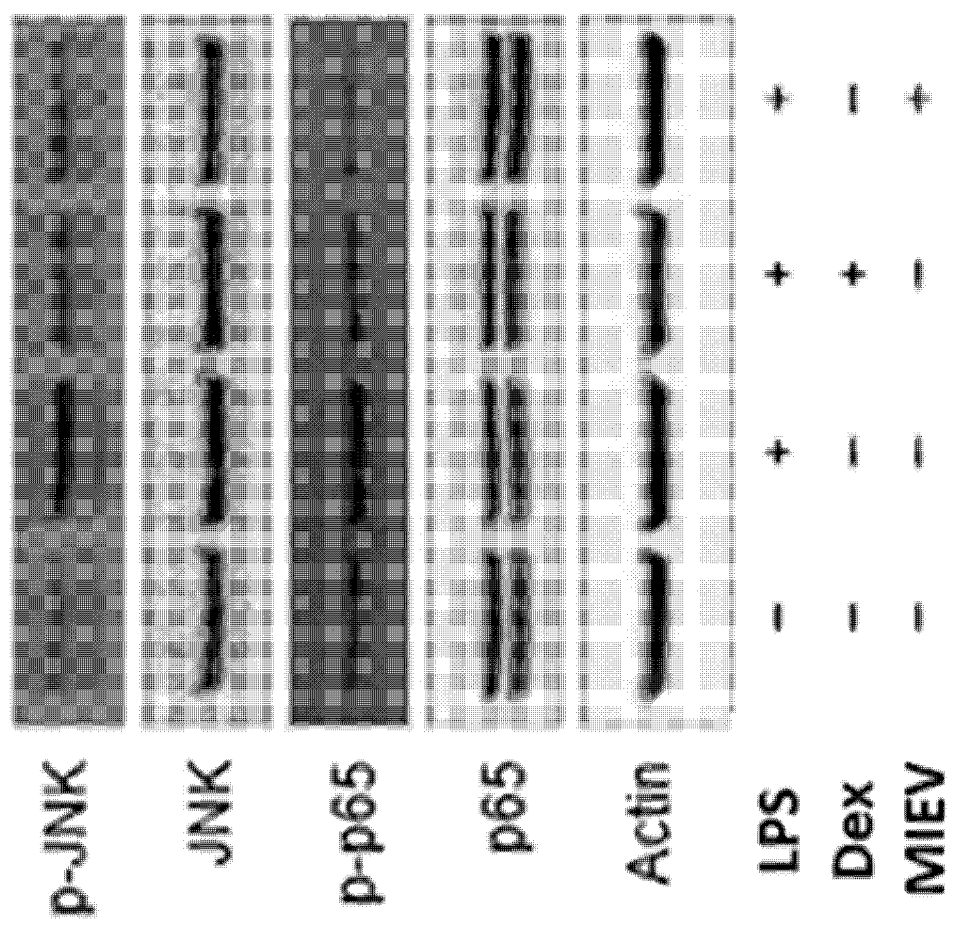
FIG. 9 is a view illustrating the results of evaluating the degree of activation of JNK and NF-kB(p65), which are signals associated with innate immunity in tissues isolated from mice administered LPS which is an inflammatory causative factor, in order to evaluate the effect of regulating innate immune function by a vesicle (MlEV) derived from *Micrococcus luteus*.

As a result, as illustrated in FIG. 9, in the group (LPS) administered LPS, phosphorylation of JNK and p65 proteins was increased compared to the negative control, which was suppressed by dexamethasone (Dex) and the vesicle (MIEV) derived from *Micrococcus luteus*. This means that the vesicles derived from *Micrococcus luteus* regulate innate immune dysfunction by efficiently suppressing the signaling pathway of JNK and NF-kB (p65) priming NLRP3 inflammasome formation.

Example 7. Regulatory Effect of Vesicles Derived from *Micrococcus luteus* on Production of Innate Immune Cells by Inflammatory Factors It has recently been revealed that ILC3 immune cells through ROR-γt signaling are important in the etiology of a neurodevelopmental disease, neurologic disease, or psychiatric disease by innate immune dysfunction for various stresses, and the cells are involved in the etiology of the disease by secreting IL-17 and the like. In particular, it has been revealed that ILC3 immune cells play a central role in the etiology of multiple sclerosis, which is a representative inflammatory neurological disease. In order to evaluate the effect of the vesicles derived from *Micrococcus luteus* on the production of ILC3 immune cells, the number of immune cells in tissue was evaluated by a flow cytometry method by administering LPS to mice by the method in Example 5.

Figure 10:
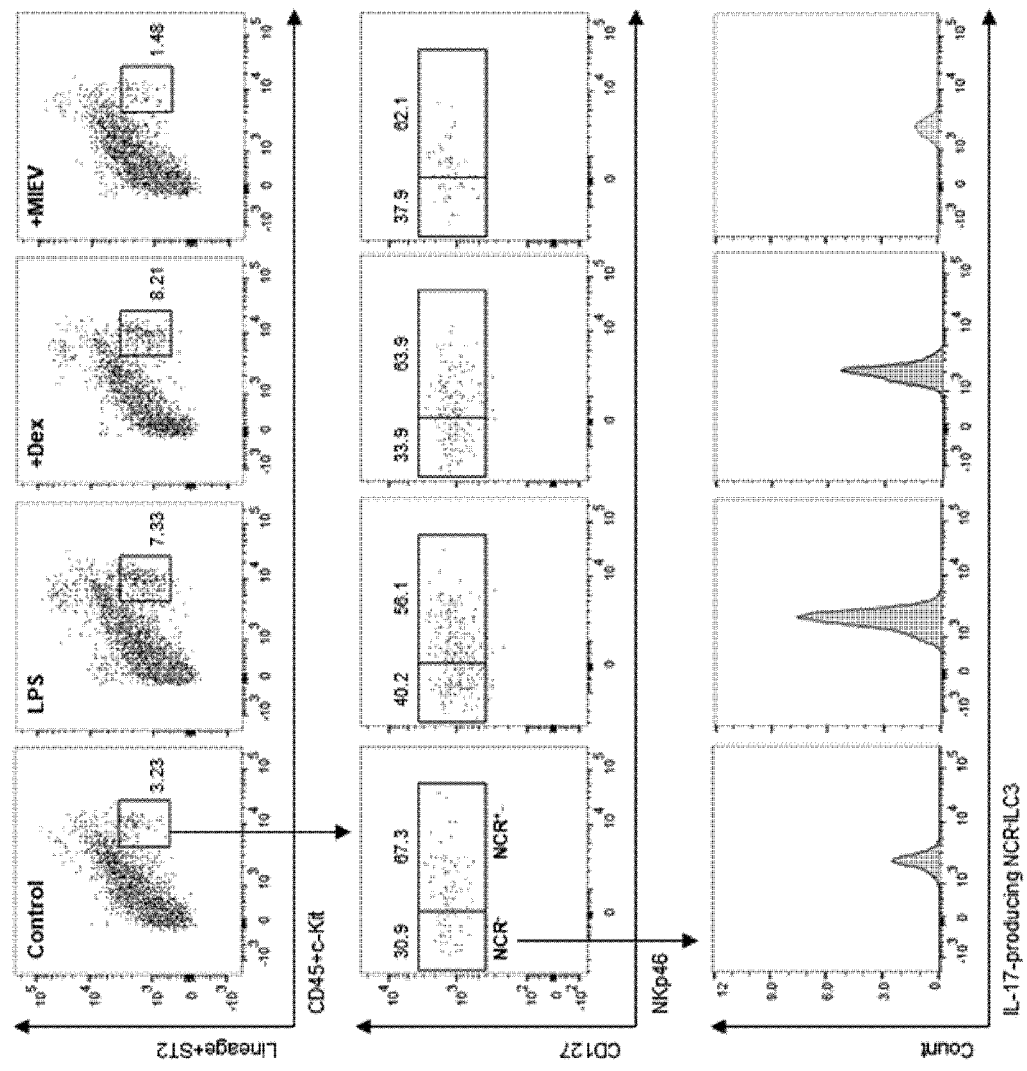
FIG. 10 is a set of views illustrating the number of type 3 innate lymphoid cells (ILC3) associated with the etiology of a neurodevelopmental disease, neurologic disease, or psychiatric disease in tissues isolated from mice administered LPS which is an inflammatory causative factor, in order to evaluate the effect of regulating the innate immune cell production of a vesicle (MlEV) derived from *Micrococcus luteus*.

As a result, as illustrated in FIG. 10, it was confirmed that in the group (LPS) administered LPS, ILC3 cells secreting IL-17 were remarkably increased compared to the negative control, the number of ILC3 cells increased by LPS was suppressed by dexamethasone (Dex) and the vesicles derived from *Micrococcus luteus* (MIEVs), and the suppression degree in the case where the vesicles were administered was even more remarkable than that in the case where dexamethansone was administered. This means that the production of innate immune cells induced by the NLRP3 inflammasome is efficiently suppressed by the vesicles derived from *Micrococcus luteus*.

Example 8. Evaluation of Efficacy of Vesicles Derived from *Micrococcus luteus* in Regulation of Cell Homeostasis by Oxidative Stress When cells are repeatedly exposed to various stresses, this is converted into oxidative stress within the cells to cause cellular senescence and death, leading to a neurodevelopmental disease, neurologic disease, or psychiatric disease. In the etiology of the neurodevelopmental disease, neurologic disease, and psychiatric disease, nitric oxide (NO) produced by endothelial NO synthase (eNOS) signals suppresses the action of reactive oxygen species (ROS), which is the main cause of oxidative stress, enhances cell homeostasis by inducing a material that enhances cell homeostasis, and suppresses cell death.

In order to evaluate the effect of the vesicles derived from *Micrococcus luteus* on cell homeostasis against oxidative stress, vascular endothelial cells were treated with the vesicles derived from *Micrococcus luteus* by the method described in Example 3, and then the degree of activation of eNOS signals was evaluated. As a method for evaluating the expression of a signaling protein, cells were lysed using a lysis buffer to extract a protein, followed by quantifying the protein using a BCA protein assay kit (Thermo, USA). The degree of protein activation was evaluated using antibodies specific for p-ERK, ERK, p-eNOS, eNOS, and (3-actin.

Figure 11:
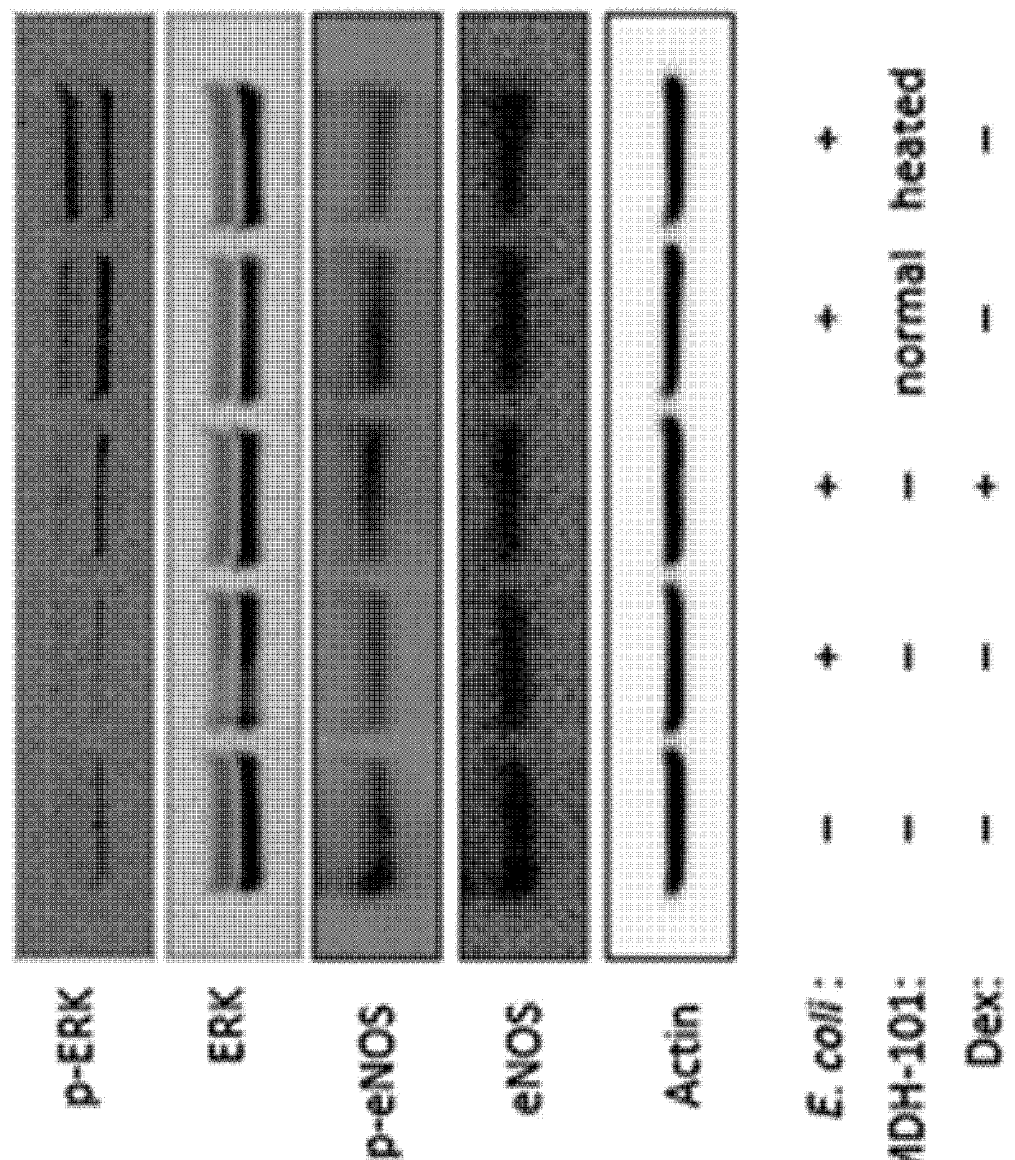
FIG. 11 is a view illustrating the results of evaluating the influence on eNOS signals suppressed by an *E. coli*-derived vesicle, which is an inflammatory causative factor by administering a vesicle (MDH-101) derived from *Micrococcus luteus* or a positive control drug dexamethasone to cells, in order to evaluate the effect of a vesicle (MDH-101) derived from *Micrococcus luteus* on eNOS signals, which are important for cell homeostasis.

As a result, as illustrated in FIG. 11, it could be confirmed that the phosphorylation of intracellular ERK and eNOS was suppressed by the *E. coli*-derived vesicle, which is an inflammatory factor, but was increased by dexamethasone (Dex) and the vesicle (MDH-101) derived from *Micrococcus luteus*. Further, it could be confirmed that the activation of eNOS by the vesicles derived from *Micrococcus luteus* was not induced when the vesicles were heat-treated. From the results, it can be seen that the vesicles derived from *Micrococcus luteus* regulate the etiology of a neurologic disease or psychiatric disease by activating eNOS and ERK signals important for vascular endothelial cell homeostasis and vascular health.

Example 9. Efficacy of Vesicles Derived from *Micrococcus luteus* in Nerve Cell Damage When neural stem cells and nerve cells are repeatedly exposed to various stresses, oxidative stress causes genetic damage in the cells, leading to aging of nerve cells and abnormal death of nerve cells. Histone deacetylase (HDAC) is involved in the deacetylation of acetylated lysine residues of various proteins, including histone proteins, to play an important role not only in the regulation of gene expression by chromatin structure and function regulation, but also in the intracellular signaling process. These HDACs are divided into Classes I, II, III and IV, and Sirtuin belonging to Class III is known as a signaling protein that maintains cell homeostasis in a low-calorie stress situation.

Among the Sirtuin proteins, Sirtuin 1 (Sirt1) is an anti-aging protein which is present in the nucleus and cytoplasm, suppresses inflammation caused by metabolic stress as a deacetylase, and increases cell survival; Sirtuin5 (Sirt5) is a protein which is present in mitochondria, has demalonylase, desuccinylase, and deacetylase enzyme functions, and maintains mitochondrial function by regulating ammonia toxicity in mitochondria; and Sirtuin 7 (Sirt7) is a protein which is present in the nucleolus in the nucleus and has a deacetylase enzyme function, and thus repairs damage to rDNA to enable the ribosome to properly produce proteins.

In order to evaluate the effect of the vesicles derived from *Micrococcus luteus* on nerve cell homeostasis against oxidative stress, nerve cells were treated with the vesicles derived from *Micrococcus luteus* by the method described in Example 3, and then the expression pattern of the sirtuin gene was evaluated, and PBS was used as a negative control. Specifically, cells were lysed using a lysis buffer and a gene was extracted, and the expression of the gene was quantified using RT-PCR. The degree of gene expression was evaluated using the primers specific for the mRNAs of the HDAC1, HDAC2, HDAC3, HDAC4, HDAC5, Sirt1, Sirt5, and Sirt7 genes shown in the following Table 1.

TABLE 1

| Name | Classification | Sequence (5'→3') | SEQ ID NO |
|---|---|---|---|
| HDAC1 | FW | CAGTGTGGCTCAGATTCCCT | 1 |
|  | RV | GGGCAGCTCATTAGGGATCT | 2 |
| HDAC2 | FW | GGGACAGGCTTGGTTGTTTC | 3 |
|  | RV | GAGCATCAGCAATGGCAAGT | 4 |
| HDAC3 | FW | AGAGAGGTCCCGAGGAGAAC | 5 |
|  | RV | ACTCTTGGGGACACAGCATC | 6 |
| HDAC4 | FW | CAATCCCACAGTCTCCGTGT | 7 |
|  | RV | CAGCACCCCACTAAGGTTCA | 8 |
| HDAC5 | FW | TGTCACCGCCAGATGTTTTG | 9 |
|  | RV | TGAGCAGAGCCGAGACACAG | 10 |
| Sirt1 | FW | GATCCTTCAGTGTCATGGTTC | 11 |
|  | RV | ATGGCAAGTGGCTCATCA | 12 |
| Sirt5 | FW | ATCGCAAGGCTGGCACCAAGAA | 13 |
|  | RV | CTAAAGCTGGGCAGATCGGACT | 14 |
| Sirt7 | FW | GAGAGCGAGGATCTGGTGAC | 15 |
|  | RV | CGTGTAGACAACCAAGTGCC | 16 |

Figure 12:
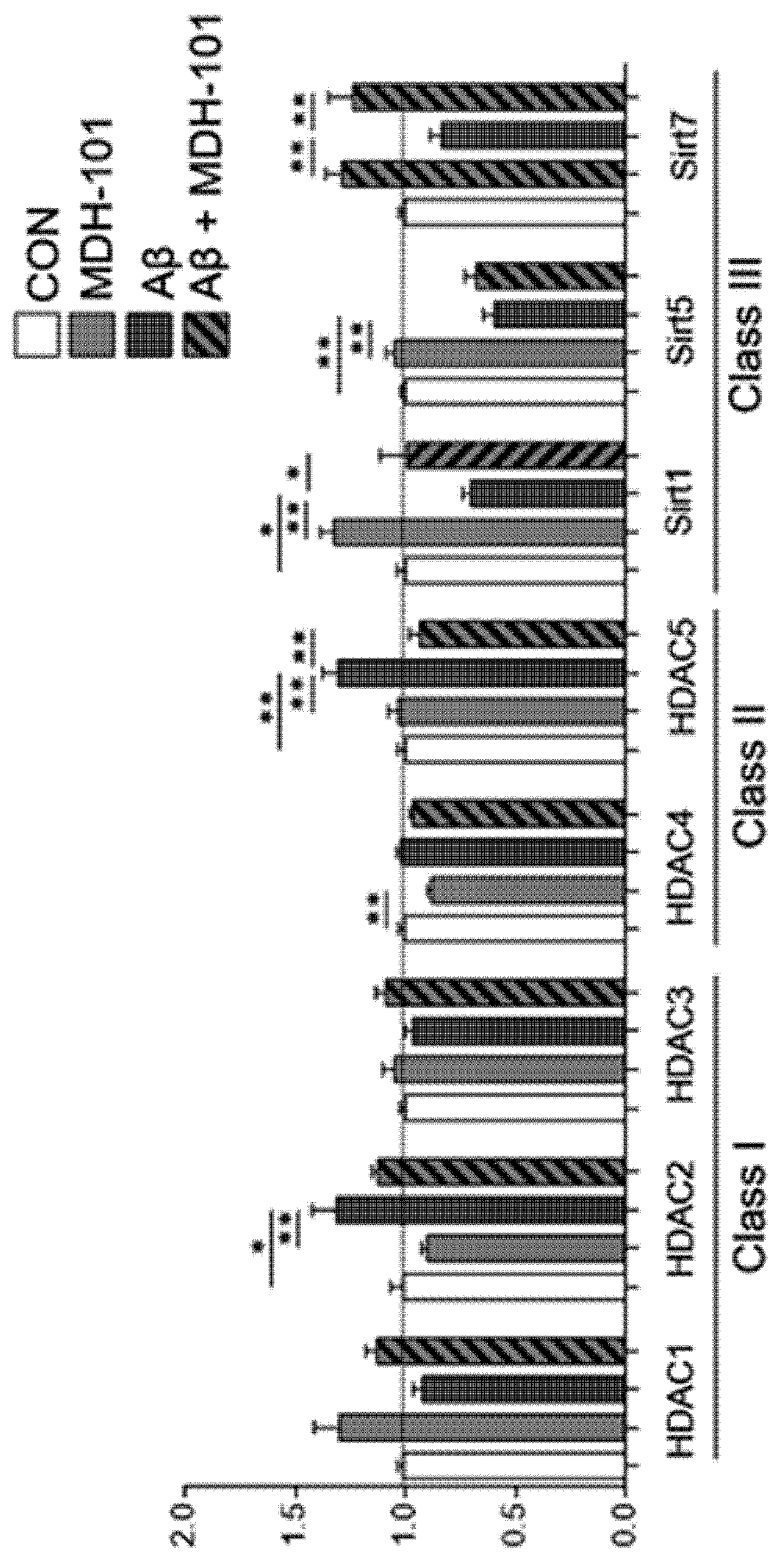
FIG. 12 is a view illustrating the results of evaluating the influence on the expression of a sirtuin gene suppressed by a causative factor beta-amyloid protein (Aβ) by administering a vesicle (MDH-101) derived from *Micrococcus luteus* and Aβ to cells, in order to evaluate the effect of a vesicle (MDH-101) derived from *Micrococcus luteus* on the expression of a sirtuin gene, which is important for cell homeostasis.

As a result, as illustrated in FIG. 12, when nerve cells were treated with an abnormal protein beta-amyloid (Aβ), the expression of HDAC2 and HDAC5 genes was significantly increased compared to the negative control, and the expression of Sirt1, Sirt5, and Sirt7 genes was decreased compared to the negative control. Further, the expression of the HDAC5 gene whose expression was increased by the Aβ protein was significantly decreased when the vesicles derived from *Micrococcus luteus* were treated, and the expression of the Sirt1 and Sirt7 genes whose expression was decreased by the Aβ protein was significantly increased when the vesicles were treated. From the results, it can be seen that the vesicles derived from *Micrococcus luteus* suppress inflammation and cell death due to metabolic stress by increasing nerve cell homeostasis through the expression of the Sirt1 and Sirt7 genes.

Example 10. Efficacy of Vesicles Derived from *Micrococcus luteus* in Suppression of Neurogenesis When neural stem cells and nerve cells are repeatedly exposed to various stresses, their neurogenesis ability deteriorates. Neurotrophins are a group of growth factor proteins which play a key role in the development of neural stem cells as well as the survival and function of differentiated nerve cells. The brains of most mammals, including humans, produce nerve cells during the fetal period, but neural stem cells are present in the hippocampus region, and thus, adult neurogenesis occurs even after birth. A brain-derived neurotrophic factor (BDNF), neurotrophin-3 (NT3), NT4/5, and a nerve growth factor (NGF) are representative neurotrophins associated with the survival and function of neural stem cells and nerve cells. Among them, the BDNF is a protein which is present in the central and peripheral nervous systems, and not only increases the survival and synaptic formation of nerve cells present in the brain and peripheral nervous system through TrkB receptors, but also induces the proliferation and differentiation of neural stem cells.

In order to evaluate the effect of the vesicles derived from *Micrococcus luteus* on the survival and function of neural stem cells and nerve cells against oxidative stress, nerve cells were treated with the vesicles derived from *Micrococcus luteus* by the method described in Example 3, and then the expression pattern of a neurotrophin and a TrkB gene which is a receptor thereof was evaluated, and PBS was used as a negative control. Specifically, cells were lysed using a lysis buffer and a gene was extracted, and the expression of the gene was quantified using RT-PCR. The degree of gene expression was evaluated using the primers specific for the mRNAs of the BDNF, NT3, NT4/5, NGF, and TrkB genes shown in the following Table 2.

TABLE 2

| Name | Classification | Sequence (5'→3') | SEQ ID NO |
|---|---|---|---|
| tBDNF | FW | TGGCTGACACTTTTGAGCAC | 17 |
|  | RV | GTTTGCGGCATCCAGGTAAT | 18 |
| NT3 | FW | TACTACGGCAACAGAGACG | 19 |
|  | RV | GTTGCCCACATAATCCTCC | 20 |
| NT4/5 | FW | GGCTCCATCCTGAACATCAT | 21 |
|  | RV | GCCATGATCTACCTGCCTGT | 22 |
| NGF | FW | AGCATTCCCTTGACACAG | 23 |
|  | RV | GGTCTACAGTGATGTTGC | 24 |
| TrkB | FW | AAGGACTTTCATCGGGAAGCTG | 25 |
|  | RV | TCGCCCTCCACACAGACAC | 26 |

Figure 13:
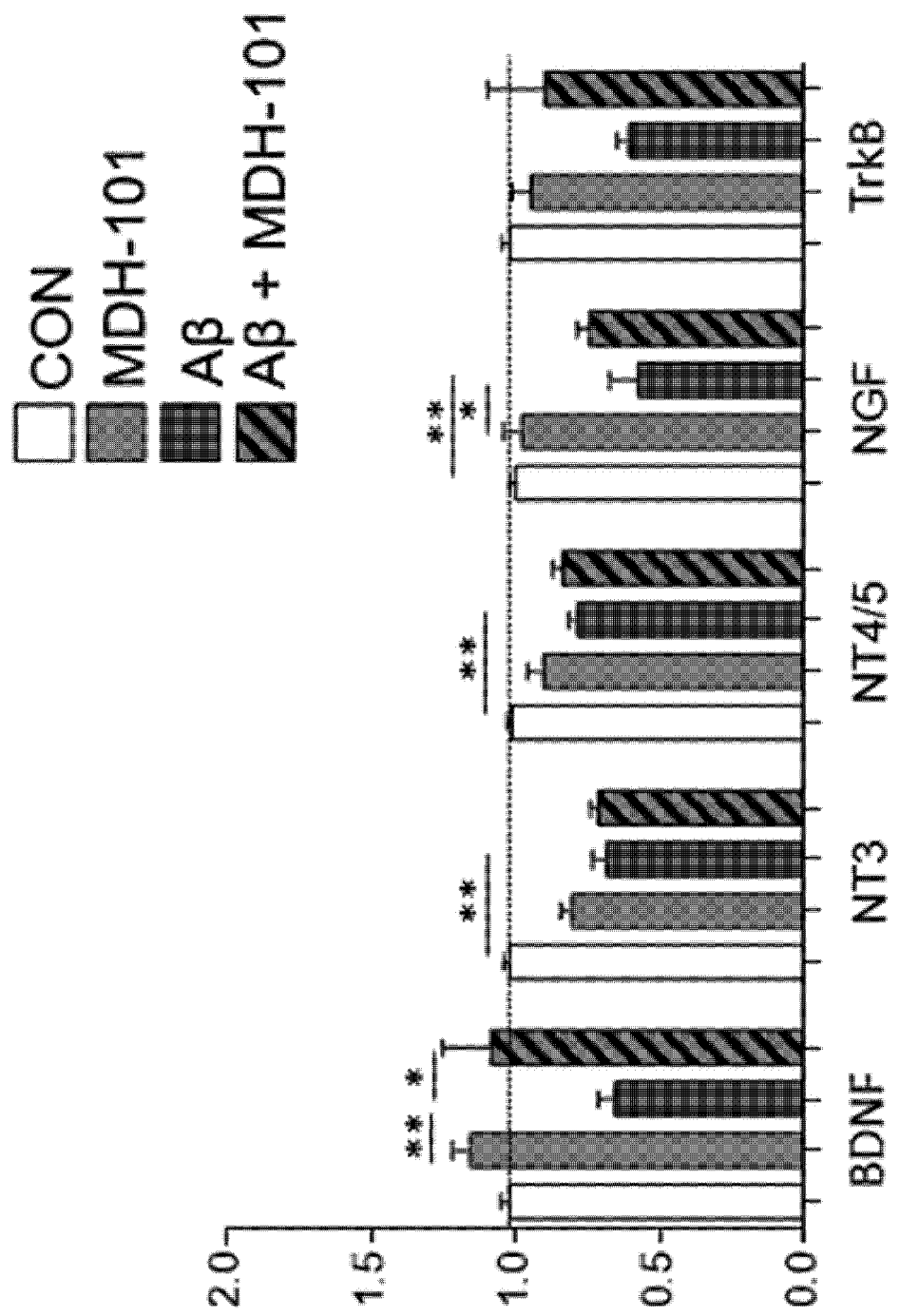
FIG. 13 is a view illustrating the results of evaluating the influence on the expression of a neurotrophin and a receptor gene suppressed by a causative factor beta-amyloid protein (Aβ) by administering a vesicle (MDH-101) derived from *Micrococcus luteus* and Aβ to cells, in order to evaluate the effect of a vesicle (MDH-101) derived from *Micrococcus luteus* on the expression of the neurotrophin and a receptor-related gene, which are important for neurogenesis.

As a result, as illustrated in FIG. 13, when nerve cells were treated with an abnormal protein beta-amyloid (Aβ), the expression of BDNF, NT3, NT45, and NGF genes was significantly reduced compared to the negative control, and among them, the expression of the BDNF gene was restored to the same extent as the negative control when the BDNF gene was treated with the vesicles derived from *Micrococcus luteus*. Further, the expression of the TrkB gene, which is a BDNF receptor, was suppressed by the Aβ protein, but restored to the level of the negative control by the vesicle. From the results, it can be seen that the vesicles derived from *Micrococcus luteus* increase the differentiation of neural stem cells and the survival and function of differentiated nerve cells by increasing BDNF and TrkB receptor gene expression.

Figure 14:
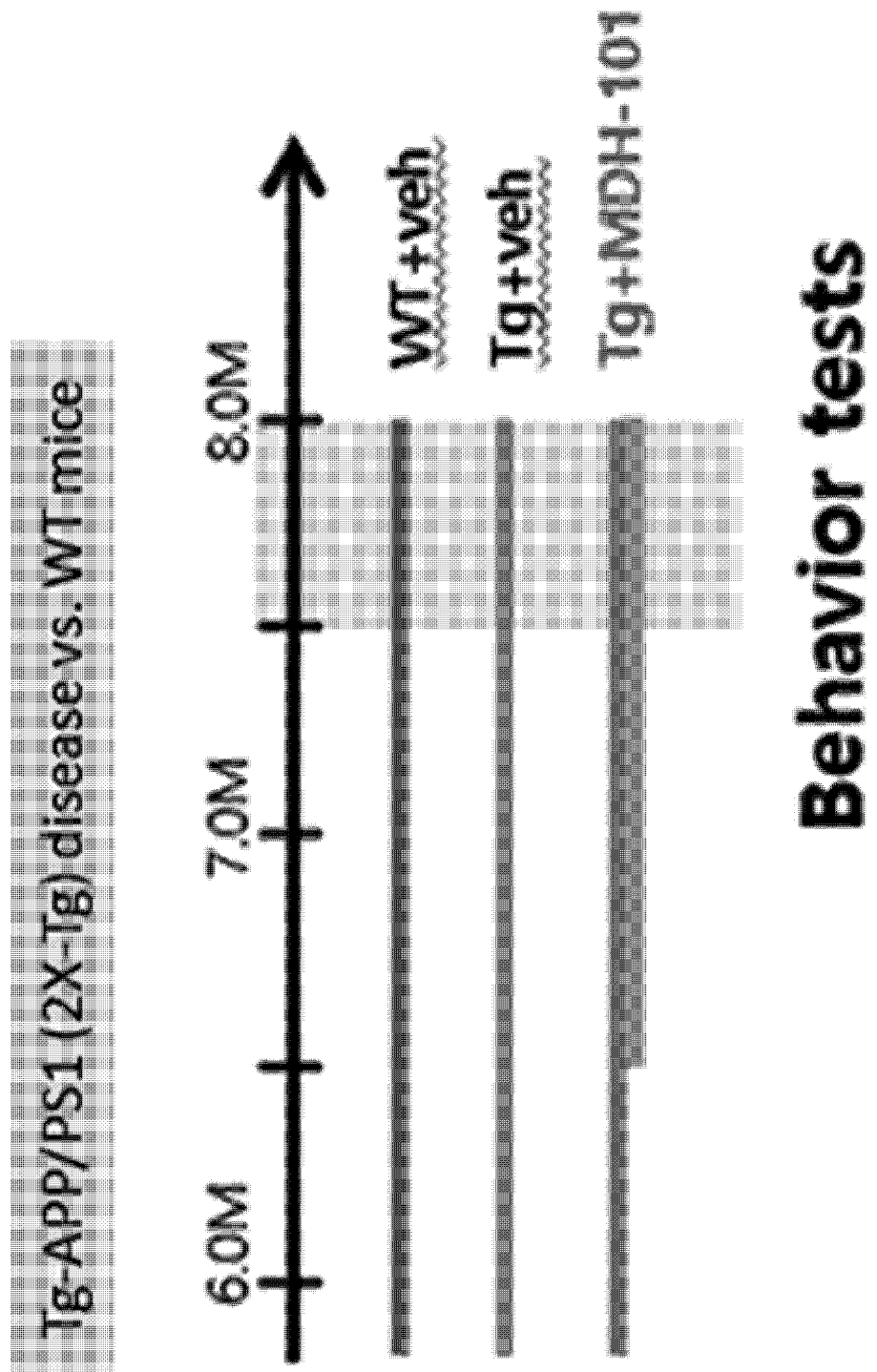
FIG. 14 is a view illustrating an experimental protocol for evaluating the therapeutic efficacy of the vesicle in a brain disease mouse model (Tg-APP/PS1 mice) orally administered a vesicle (MDH-101) derived from *Micrococcus luteus* (WT+veh: a normal mouse group, Tg+veh: a brain disease mouse group, Tg+MDH-101: a mouse group obtained by orally administering a vesicle (MDH-101) derived from *Micrococcus luteus* to a brain disease mouse model, Hereinafter the same).

Example 11. Cognitive Function Improving Effect of Vesicles Derived from *Micrococcus luteus* in Brain Disease Mouse Model A Tg-APP/PS1 mouse is a mouse model in which a brain disease is induced by overexpressing abnormal amyloid precursor protein (APP) and PS1 (presenilin 1) proteins, and is an animal model in which the deposition of an abnormal protein plaque which can be histologically detected from 6.5 months of age is exhibited and cognitive dysfunction is reliably detected at the age of 7 to 8 months. In order to evaluate the cognitive function improving effect of the vesicles derived from *Micrococcus luteus*, as illustrated in FIG. 14 using the mouse model, behavioral tests and histological tests were performed by dividing the mice into a normal mouse group (WT+veh), a sham-treated brain disease mouse group (Tg+veh), and a brain disease mouse group (Tg+MDH-101) in which 50 µg/mouse of the vesicles derived from *Micrococcus luteus* were orally administered to a brain disease mouse model.

Figure 15:
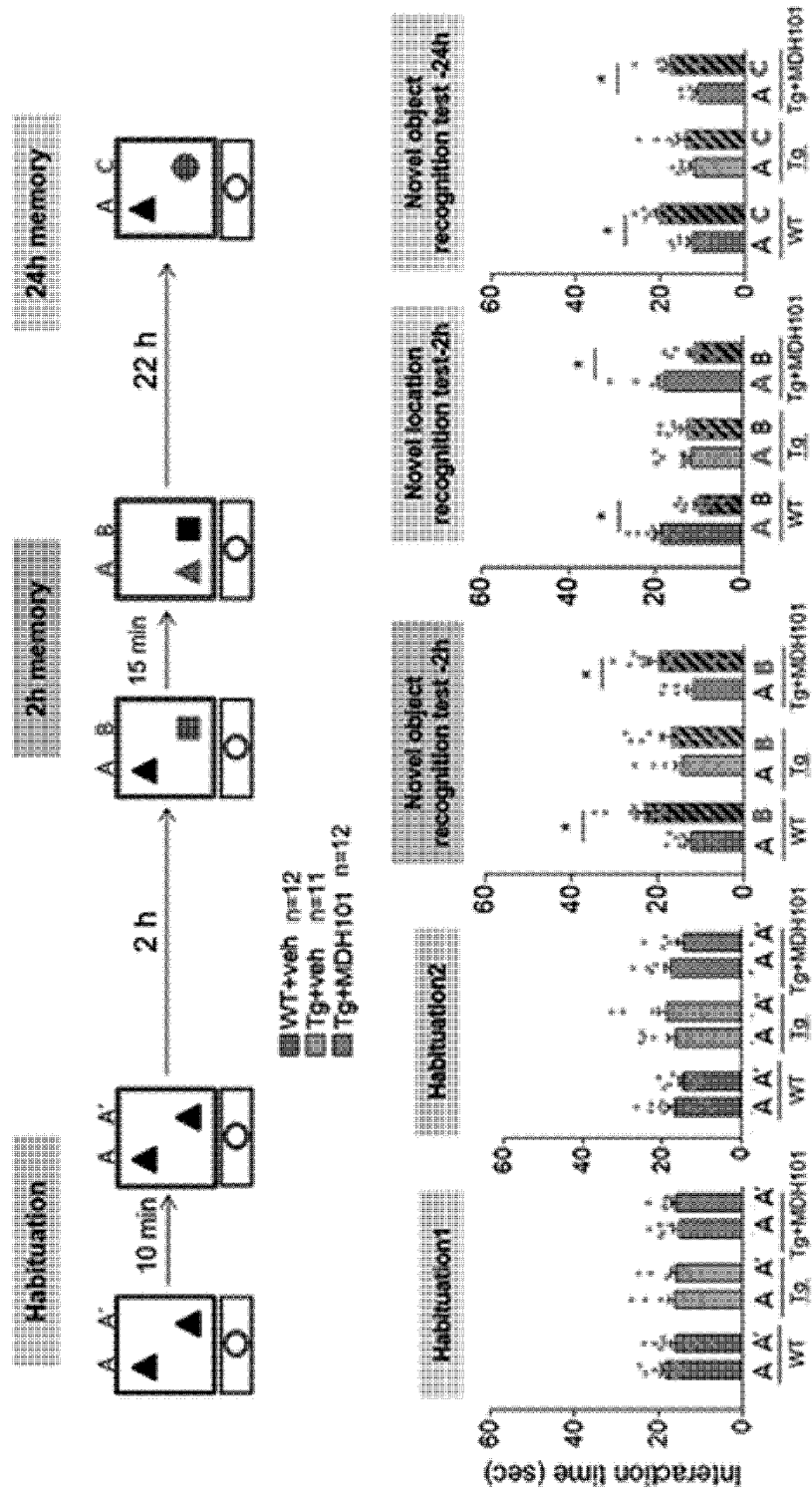
FIG. 15 is a set of views illustrating the therapeutic efficacy of a vesicle (MDH-101) derived from *Micrococcus luteus* for cognitive function in a Tg-APP/PS1 brain disease mouse model by means of a novel object/location recognition test.

In order to evaluate the cognitive function improving effect of the vesicles derived from *Micrococcus luteus*, as illustrated in FIG. 15, each group of WT+veh, Tg+veh, and Tg+MDH-101 was exposed to a repositioned object or a novel object, and the time to search for the object was measured for 10 minutes. As a result, as illustrated in FIG. 15, it was confirmed that in a novel object recognition test measured after 2 or 24 hours, it took a long time for the WT+veh and Tg+MDH-101 groups to find the novel object, but there was no change in the Tg+veh group. In addition, it was confirmed that even in a novel location recognition test, it took a long time for the WT+veh and Tg+MDH-101 groups to find the repositioned object, but there was no change in the Tg+veh group. This means that the vesicles derived from *Micrococcus luteus* suppress the progression of short-term and long-term cognitive dysfunction in brain disease mice induced by the production of an abnormal protein.

Example 12. Learning Ability Improving Effect of Vesicles Derived from *Micrococcus luteus* in Brain Disease Mouse Model In order to evaluate the learning ability improving efficacy of the vesicles derived from *Micrococcus luteus* in the brain disease mouse model in Example 11, as illustrated in FIG. 16A, an evaluation in which a hidden platform is searched for after training mice to search for the hidden platform in a water bottle for 5 days was performed.

Figure 16:
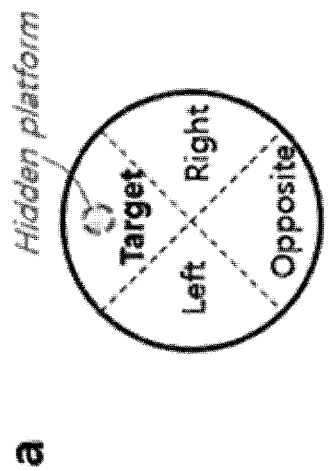
FIG. 16 illustrates the results of evaluating the therapeutic efficacy of a vesicle (MDH-101) derived from *Micrococcus luteus* for leaning ability in a Tg-APP/PS1 brain disease mouse model by a water maze test using the *Micrococcus luteus*-derived vesicles, (A) is a view illustrating a protocol of the water maze test, (B) is a view illustrating the results of showing the time to find a hidden platform during a 5-day study period, and (C) is a view illustrating the time when mice stayed in each part of a water bottle.
Figure 16:
Figure 16:
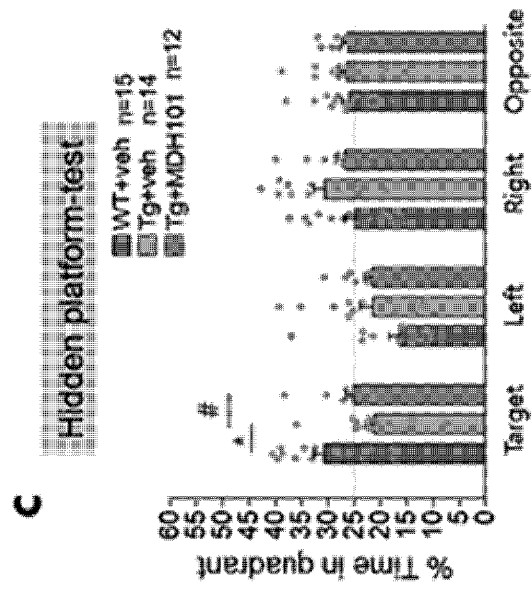

As a result, as illustrated in FIG. 16B, the WT+veh group had the fastest time to find the hidden platform during the 5-day training period, and the Tg+MDH-101 group administered the vesicles derived from *Micrococcus luteus* showed a learning ability similar to that of the WT+veh group, but the Tg−veh group showed the slowest learning time. Furthermore, as illustrated in FIG. 16C, in terms of time to find the hidden platform and stay, the WT+veh group stayed in the platform position for a long time, and the Tg+MDH-101 group administered the vesicles derived from *Micrococcus luteus* stayed a significantly longer time at the platform position than the Tg−veh group. From the above results, it can be seen that the vesicles derived from *Micrococcus luteus* have a therapeutic effect on spatial perceptual learning and memory ability restoration in mice with brain disease.

Example 13. Memory Ability Improving Effect of Vesicles Derived from *Micrococcus luteus* in Brain Disease Mouse Model In order to evaluate the memory ability improving effect of the vesicles derived from *Micrococcus luteus* in the brain disease mouse model in Example 11, as illustrated in FIG. 17A, a test was performed to confirm whether mice remembered associated fear/anxiety for a long period of time of 24, 72, and 120 hours after making the mice learn fear and anxiety associated with chamber context by applying an electric shock to the paws of the mice when the mice entered a dark chamber.

Figure 17:
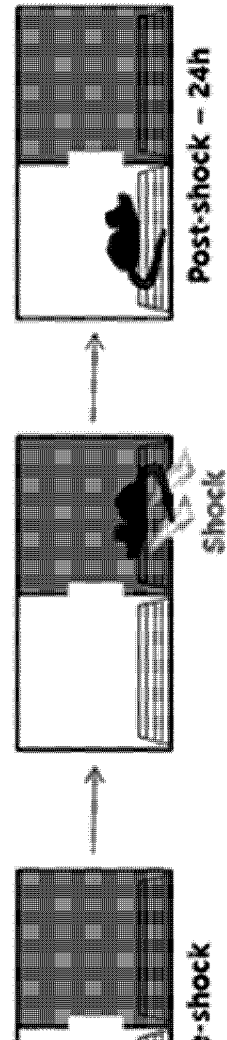
FIG. 17 illustrates the results of evaluating the therapeutic efficacy of a vesicle (MDH-101) derived from *Micrococcus luteus* for memory ability improving in a Tg-APP/PS1 brain disease mouse model by a passive avoidance test, (A) is a view illustrating a passive avoidance test protocol, (B) is a view illustrating the results of measuring the time taken for a mouse subjected to an electric shock to re-enter a dark chamber when entering the dark chamber, and (C) is a view illustrating the freezing time of a mouse after being subjected to an electric shock.
Figure 17:
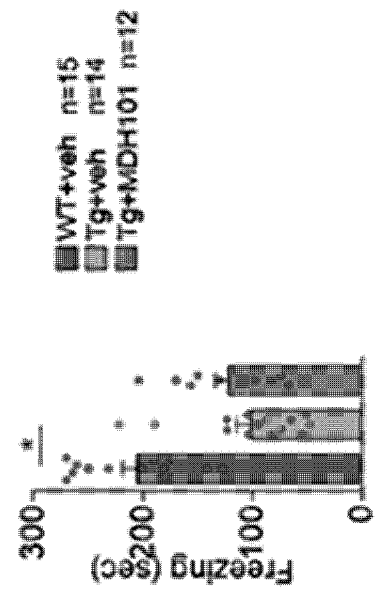
Figure 17:
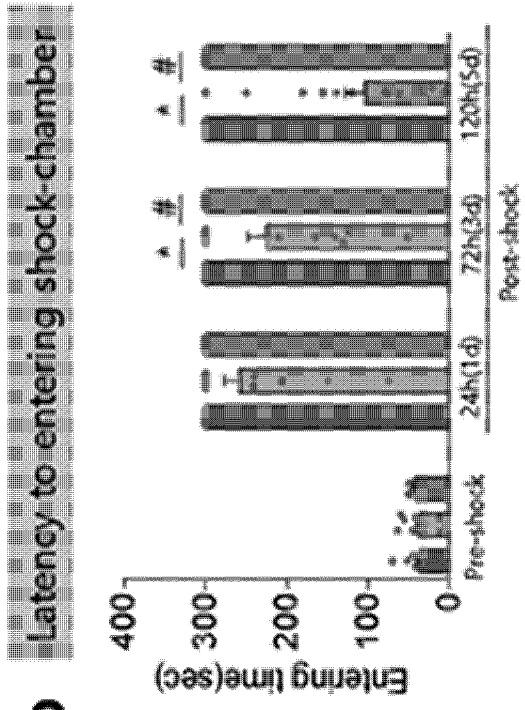

As a result, as illustrated in FIG. 17B, it could be confirmed that mice in the WT+veh and Tg+MDH-101 groups did not enter the dark chamber until 300 seconds had passed during the experiment at the time point of 24, 72, and 120 hours, whereas mice in the Tg+veh group were entering the dark chamber faster and faster. Further, as illustrated in FIG. 17C, it could be confirmed that when mice entered the dark chamber, were subjected to an electric shock, and exited the dark chamber, in terms of the freezing time due to the shock, mice in the WT+veh group had a significantly longer freezing time than mice in the Tg+veh group, whereas mice in the Tg+MDH-101 group administered the vesicles derived from *Micrococcus luteus* had a significant difference from the mice in the Tg+veh group. From the results, it can be seen that the vesicles derived from *Micrococcus luteus* have the effect of suppressing memory ability loss induced by the abnormal protein.

Example 14. Evaluation of Efficacy of Vesicles Derived from *Micrococcus luteus* on Formation of Abnormal Plaque in Brain Disease Mouse Model Amyloid beta (Aβ) plaque is a protein representatively found in the brain of a patient with Alzheimer's disease, and in a Tg-APP/PS1 model, it is known that the Aβ plaque begins to accumulate in the mouse brain and induces Alzheimer's symptoms. Aβ plaques deposited in brain tissue were analyzed by performing fluorescence staining with a Thioflavin-S dye on brain sections of the mouse models in Example 11.

Figure 18:
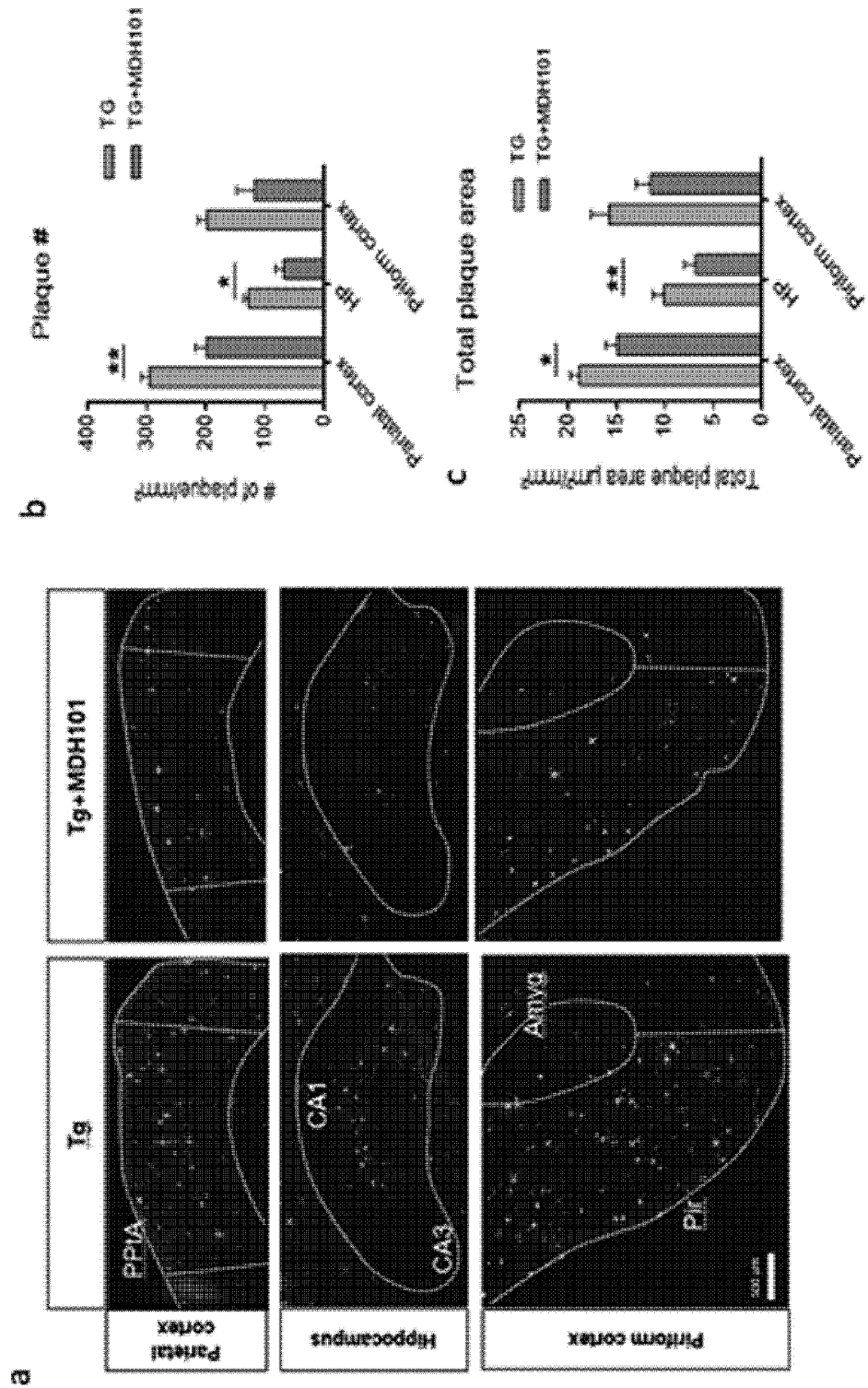
FIG. 18 illustrates the results of comparing amyloid-beta (Aβ) plaque fluorescence staining images and quantitative data in the parietal cortex, hippocampus, and piriform cortex regions of a Tg-APP/PS1 brain disease mouse model, and is a view illustrating (A) A3 plaque staining photos, (B) the number of A3 plaques per unit area, and (C) the area of A3 plaques per unit area in the parietal cortex, hippocampus, and piriform cortex of a Tg+veh group (TG) and a Tg+MDH-101 group.

As a result, as illustrated in FIG. 18A, it could be confirmed that Aβ plaques formed in the parietal cortex, hippocampus, and piriform cortex regions of the brain had a difference between the Tg+veh group and the Tg+MDH-101 group administered the vesicles derived from *Micrococcus luteus*. In addition, as illustrated in FIGS. 18B and 18C, it could be confirmed that, compared to the Tg+veh group, the Tg+MDH-101 group administered the vesicles derived from *Micrococcus luteus* had significantly decreased number (FIG. 18B) and area (FIG. 18C) of Aβ plaques per unit area deposited in the parietal cortex and hippocampus regions. From the results, it can be seen that the vesicles derived from *Micrococcus luteus* have the effect of suppressing the formation of abnormal protein plaques in a brain disease mouse model caused by the overexpression of an abnormal protein.

Example 15. Evaluation of Adult Neurogenesis Efficacy of Vesicles Derived from *Micrococcus luteus* in Brain Disease Mouse Model Based on the above examples, in order to elucidate a mechanism that suppresses the deterioration of nerve function shown in a brain disease mouse model to which the vesicles derived from *Micrococcus luteus* were administered, neurogenesis was evaluated.

Figure 19:
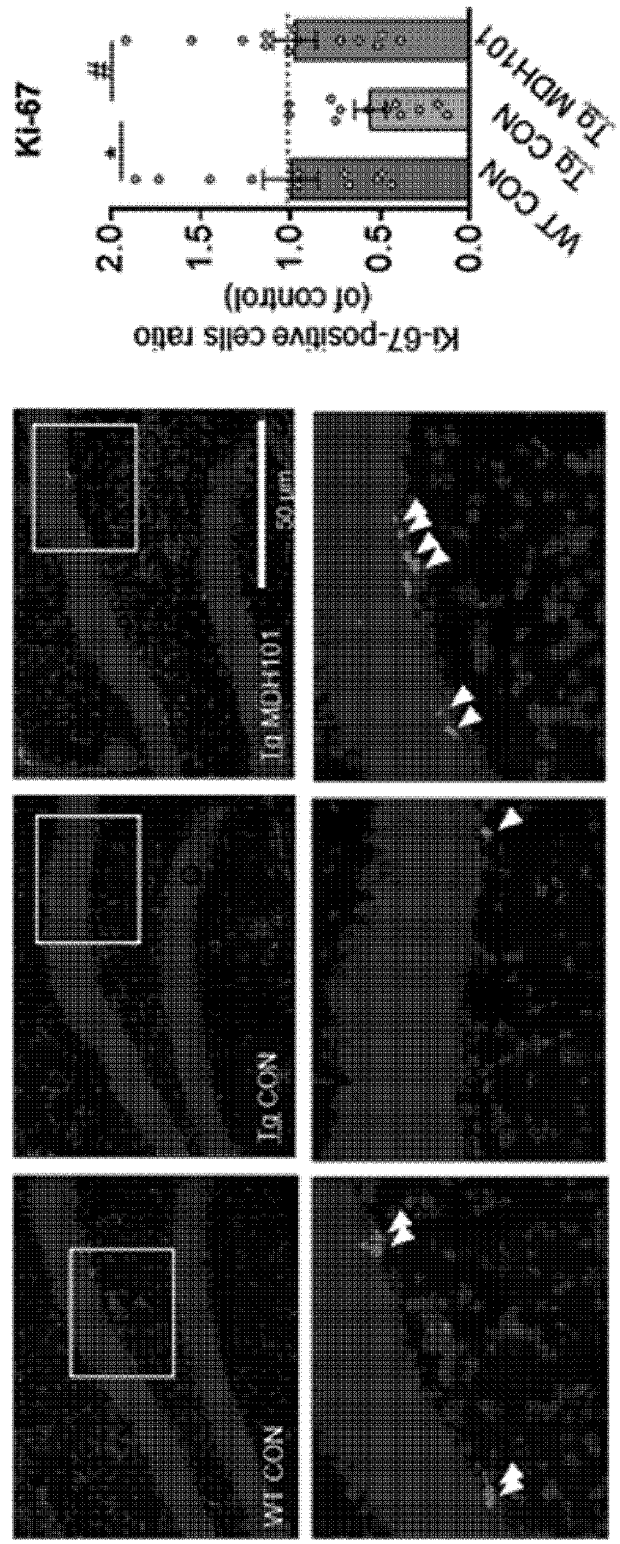
FIG. 19 illustrates the results of confirming the therapeutic efficacy of a vesicle (MDH-101) derived from *Micrococcus luteus* for the proliferation of neural stem cells in the hippocampus of a Tg-APP/PS1 brain disease mouse model by staining the expression of Ki-67, which is a marker for initial neurogenesis in the brain, the left side is a view illustrating the Ki-67 staining results, and the right side is a view illustrating the ratio of the number of cells stained with Ki-67 in the Tg+veh group and the Tg+MDH-101 group relative to a normal mouse group (WT+veh) (WT CON: the normal mouse group, and TG CON: the brain mouse group, hereinafter the same).

As illustrated in FIG. 19, as a result of confirming the number of cells stained with Ki-67 by fluorescence staining of Ki-67 known as a marker for neural stem cell proliferation, it could be confirmed that the number of cells stained with Ki-67 was significantly reduced in the Tg+veh group compared to the WT+veh group. In contrast, it could be confirmed that the Tg+MDH-101 group to which the vesicles derived from *Micrococcus luteus* were administered had a significantly increased number of cells stained with Ki-67 compared to the Tg+veh group, and recovery to an extent similar to the WT+veh group was achieved.

Figure 20:
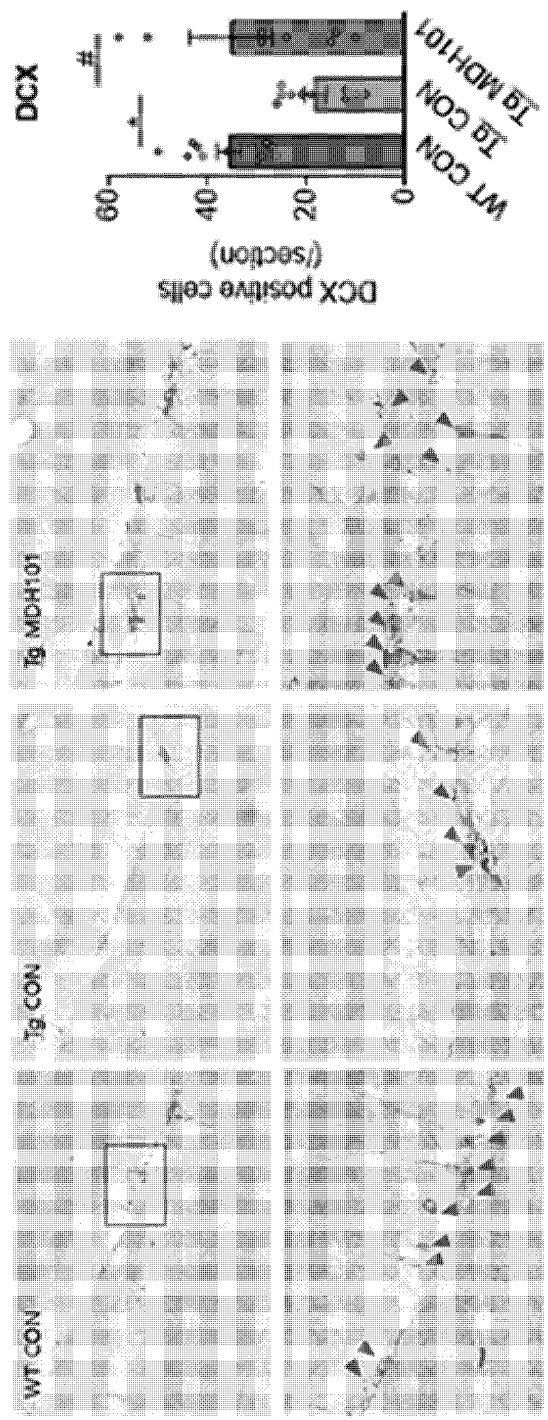
FIG. 20 illustrates the results of evaluating the therapeutic efficacy of a vesicle (MDH-101) derived from *Micrococcus luteus* for the differentiation and migration of neural stem cells in the hippocampus of a Tg-APP/PS1 brain disease mouse model by staining with doublecortin (DCX), which is a marker associated with the differentiation and migration of neural stem cells, the left side is a view illustrating the results of staining with DCX, and the right side is a view illustrating the average number of cells stained with DCX.

Furthermore, in order to evaluate the efficacy of the vesicles derived from *Micrococcus luteus* in the differentiation and migration of neural stem cells, neural stem cells were subjected to fluorescence staining with double cortin (DCX), which is a marker associated with the differentiation and migration of neural stem cells. As a result, as illustrated in FIG. 20, it could be confirmed that the number of DCX-positive cells in the Tg+veh group was significantly decreased compared to the WT+veh group, which was significantly restored in the Tg+MDH-101 group administered the vesicles derived from *Micrococcus luteus*. From the results, it can be seen that the vesicles derived from

*Micrococcus luteus* induce neurogenesis, and exhibits the effect of treating a neurodevelopmental disease, neurologic disease, or psychiatric disease by the production of an abnormal protein by producing neurogenesis in a brain disease mouse model.

Example 16. Evaluation of Ability of Vesicles Derived from *Micrococcus Luteus* to Produce Nerve Cell Dendrites in Brain Disease Mouse Model Based on the above examples, in order to elucidate an action mechanism for the improvement in nerve function shown in a degenerative brain disease mouse model to which vesicles derived from *Micrococcus luteus* were administered, the ability of nerve cells to form dendrites (dendritic process) was evaluated. Since changes in the morphology and number of dendrites are important for signaling between nerve cells, the changes were evaluated using the expression of microtubule-associated protein 2 (MAP2), which is well known as a nerve cell-specific cytoskeletal protein.

Figure 21:
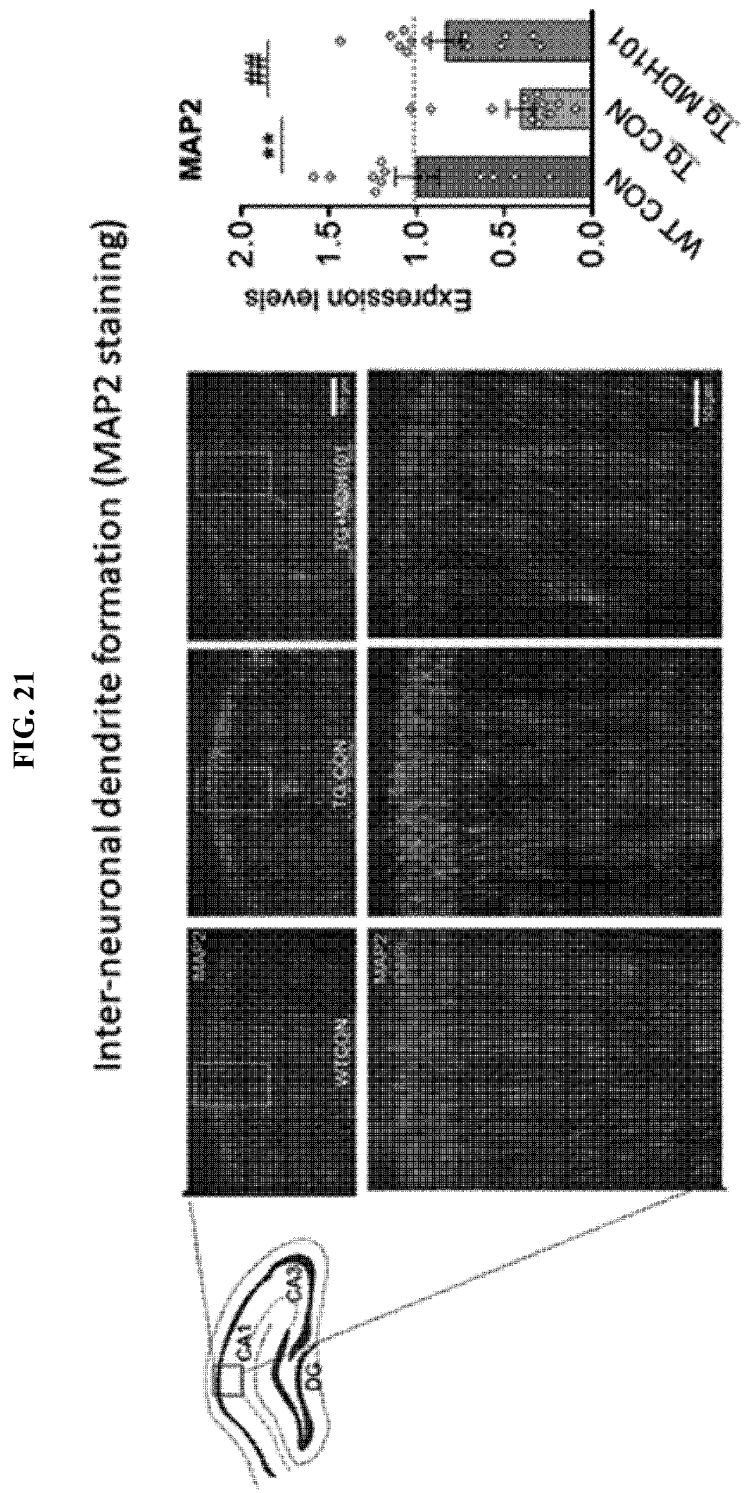
FIG. 21 illustrates the results of evaluating the therapeutic efficacy of a vesicle (MDH-101) derived from *Micrococcus luteus* for dendrite formation of nerve cells in the hippocampus of a Tg-APP/PS1 brain disease mouse model by staining brain tissue nerve cells with MAP2, the left side is a view illustrating the results of staining with MAP2, and the right side is a view illustrating the expression level of MAP2.

As a result, as illustrated in FIG. 21, it could be confirmed that the expression of MAP2 in the Tg+veh group was significantly decreased compared to the WT+veh group, which was significantly restored in the Tg+MDH-101 group administered the vesicles derived from *Micrococcus luteus*. From the results, it can be seen that the vesicles derived from *Micrococcus luteus* regulate the onset or course of a neurodevelopmental disease, neurologic disease, or psychiatric disease by increasing the inter-neuronal integrity through the formation of nerve cell dendrites.

From the results, it can be seen that the vesicles derived from *Micrococcus luteus* of the present invention efficiently suppress the onset or course of the neurodevelopmental disease, neurologic disease, or psychiatric disease. In particular, it can be seen that the vesicle suppresses the abnormal death of neural stem cells and nerve cells by regulating the formation of a NLRP3 inflammasome, a signaling material associated with immunity, which is essential for a neurodevelopmental disease, neurologic disease, or psychiatric disease. Furthermore, it can be seen that the vesicle can induce the production of NO which is a key signaling material for cell homeostasis by activating eNOS signaling, enhance the homeostasis of neural stem cells and nerve cells by restoring the expression of sirtuin 1 and sirtuin 7 suppressed by oxidative stress, and efficiently treat a neurodevelopmental disease, neurologic disease, and psychiatric disease by increasing not only the proliferation and differentiation of neural stem cells and the survival and inter-neuronal integrity of nerve cells.

Therefore, the vesicles derived from *Micrococcus luteus* of the present invention are expected to be able to be used for alleviating, preventing, or treating a neurodevelopmental disease, neurologic disease, or psychiatric disease.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

The present inventors confirmed that when vesicles derived from *Micrococcus luteus* were orally administered, the vesicles were absorbed into blood vessels and distributed in brain tissue. Further, the present inventors confirmed that when epithelial cells and inflammatory cells were treated with the vesicles, the secretion of inflammatory mediators by pathogenic factors was remarkably suppressed, and when cells were treated with the vesicles, NLRP3 protein expression and NF-kB(p65) signals induced by pathogenic factors were suppressed. In addition, the present inventors confirmed that when cells were treated with the vesicles, eNOS signals suppressed by pathogenic factors were increased. Furthermore, the present inventors confirmed that when neurological cells were treated with the vesicles, the expression of a BDNF gene suppressed by pathogenic factors was restored. Further, the present inventors confirmed that when neurological cells were treated with the vesicles, the expression of sirtuin 1 and sirtuin 7 genes suppressed by pathogenic factors was restored. In addition, the present inventors confirmed that when the vesicles were administered to a neurologic disease mouse model, cognitive function was significantly restored. Furthermore, the present inventors confirmed that when the vesicles were administered to the neurologic disease mouse model, neurogenesis was significantly restored, so that the vesicles derived from *Micrococcus luteus* according to the present invention may be usefully used for the development of a medicine, health functional food, or the like for preventing a neurodevelopmental disease, a neurological disorder, or a psychiatric disease, alleviating symptoms thereof, or treating the disorders, and will be able to be usefully used as a drug delivery system for treating the neurodevelopmental disease, the neurologic disease, or the psychiatric disease.

The invention claimed is:

1. A method for alleviating or treating symptoms of a degenerative brain neurologic disease in a subject in need thereof, comprising administering a composition comprising vesicles derived from *Micrococcus luteus* as an active ingredient to the subject having the symptoms,
   wherein the disease is mediated by a NLR family pyrin domain containing 3 inflammasome (NLRP3 inflammasome),
   wherein the composition suppresses NLRP3 inflammasome formation,
   wherein the alleviating or treating symptoms is selected from the group consisting of suppression of progression of short-term and long-term cognitive impairments, restoration of spatial perceptual learning or memory, restoration of memory ability, suppressing memory ability loss induced by abnormal beta-amyloid (Aβ) protein, suppression of accumulated Aβ plaque, induction of neurogenesis, and protection of microstructure of dendrites to improve intercellular integrity, and
   wherein the degenerative brain neurologic disease is one or more diseases selected from the group consisting of Alzheimer's disease, Parkinson's disease, amyotrophic lateral sclerosis, Huntington's disease, and epilepsy.

2. The method of claim 1, wherein the degenerative brain neurologic disease is due to neurogenesis dysfunction.

3. The method of claim 1, wherein the vesicles have an average diameter of 10 to 200 nm.

4. The method of claim 1, wherein the vesicles are naturally secreted or artificially produced from *Micrococcus luteus*.

5. The method of claim 1, wherein the composition is a pharmaceutical composition, a food composition, or an inhalant composition.

\* \* \* \* \*

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: HDAC1_F

<400> SEQUENCE: 1
cagtgtggct cagattccct                                           20

<210> SEQ ID NO 2
<211> LENGTH: 20

```
<212> TYPE: DNA
<213> ORGANISM: Artificial Sequence
<220> FEATURE:
<223> OTHER INFORMATION: HDAC1_R

<400> SEQUENCE: 2
gggcagctca ttagggatct                                              20

<210> SEQ ID NO 3
<211> LENGTH: 20
<212> TYPE: DNA
<213> ORGANISM: Artificial Sequence
<220> FEATURE:
<223> OTHER INFORMATION: HDAC2_F

<400> SEQUENCE: 3
gggacaggct tggttgtttc                                              20

<210> SEQ ID NO 4
<211> LENGTH: 20
<212> TYPE: DNA
<213> ORGANISM: Artificial Sequence
<220> FEATURE:
<223> OTHER INFORMATION: HDAC2_R

<400> SEQUENCE: 4
gagcatcagc aatggcaagt                                              20

<210> SEQ ID NO 5
<211> LENGTH: 20
<212> TYPE: DNA
<213> ORGANISM: Artificial Sequence
<220> FEATURE:
<223> OTHER INFORMATION: HDAC3_F

<400> SEQUENCE: 5
agagaggtcc cgaggagaac                                              20

<210> SEQ ID NO 6
<211> LENGTH: 20
<212> TYPE: DNA
<213> ORGANISM: Artificial Sequence
<220> FEATURE:
<223> OTHER INFORMATION: HDAC3_R

<400> SEQUENCE: 6
actcttgggg acacagcatc                                              20

<210> SEQ ID NO 7
<211> LENGTH: 20
<212> TYPE: DNA
<213> ORGANISM: Artificial Sequence
<220> FEATURE:
<223> OTHER INFORMATION: HDAC4_F

<400> SEQUENCE: 7
caatcccaca gtctccgtgt                                              20

<210> SEQ ID NO 8
<211> LENGTH: 20
<212> TYPE: DNA
<213> ORGANISM: Artificial Sequence
<220> FEATURE:
<223> OTHER INFORMATION: HDAC4_R

<400> SEQUENCE: 8
```

| | |
|---|---|
| cagcaccca ctaaggttca | 20 |

<210> SEQ ID NO 9
<211> LENGTH: 20
<212> TYPE: DNA
<213> ORGANISM: Artificial Sequence
<220> FEATURE:
<223> OTHER INFORMATION: HDAC5_F

<400> SEQUENCE: 9

| | |
|---|---|
| tgtcaccgcc agatgttttg | 20 |

<210> SEQ ID NO 10
<211> LENGTH: 20
<212> TYPE: DNA
<213> ORGANISM: Artificial Sequence
<220> FEATURE:
<223> OTHER INFORMATION: HDAC5_R

<400> SEQUENCE: 10

| | |
|---|---|
| tgagcagagc cgagacacag | 20 |

<210> SEQ ID NO 11
<211> LENGTH: 21
<212> TYPE: DNA
<213> ORGANISM: Artificial Sequence
<220> FEATURE:
<223> OTHER INFORMATION: Sirt1_F

<400> SEQUENCE: 11

| | |
|---|---|
| gatccttcag tgtcatggtt c | 21 |

<210> SEQ ID NO 12
<211> LENGTH: 18
<212> TYPE: DNA
<213> ORGANISM: Artificial Sequence
<220> FEATURE:
<223> OTHER INFORMATION: Sirt1_R

<400> SEQUENCE: 12

| | |
|---|---|
| atggcaagtg gctcatca | 18 |

<210> SEQ ID NO 13
<211> LENGTH: 22
<212> TYPE: DNA
<213> ORGANISM: Artificial Sequence
<220> FEATURE:
<223> OTHER INFORMATION: Sirt5_F

<400> SEQUENCE: 13

| | |
|---|---|
| atcgcaaggc tggcaccaag aa | 22 |

<210> SEQ ID NO 14
<211> LENGTH: 22
<212> TYPE: DNA
<213> ORGANISM: Artificial Sequence
<220> FEATURE:
<223> OTHER INFORMATION: Sirt5_R

<400> SEQUENCE: 14

| | |
|---|---|
| ctaaagctgg gcagatcgga ct | 22 |

<210> SEQ ID NO 15
<211> LENGTH: 20
<212> TYPE: DNA
<213> ORGANISM: Artificial Sequence

```
<220> FEATURE:
<223> OTHER INFORMATION: Sirt7_F

<400> SEQUENCE: 15
gagagcgagg atctggtgac                                              20

<210> SEQ ID NO 16
<211> LENGTH: 20
<212> TYPE: DNA
<213> ORGANISM: Artificial Sequence
<220> FEATURE:
<223> OTHER INFORMATION: Sirt7_R

<400> SEQUENCE: 16
cgtgtagaca accaagtgcc                                              20

<210> SEQ ID NO 17
<211> LENGTH: 20
<212> TYPE: DNA
<213> ORGANISM: Artificial Sequence
<220> FEATURE:
<223> OTHER INFORMATION: tBDNF_F

<400> SEQUENCE: 17
tggctgacac ttttgagcac                                              20

<210> SEQ ID NO 18
<211> LENGTH: 20
<212> TYPE: DNA
<213> ORGANISM: Artificial Sequence
<220> FEATURE:
<223> OTHER INFORMATION: tBDNF_R

<400> SEQUENCE: 18
gtttgcggca tccaggtaat                                              20

<210> SEQ ID NO 19
<211> LENGTH: 19
<212> TYPE: DNA
<213> ORGANISM: Artificial Sequence
<220> FEATURE:
<223> OTHER INFORMATION: NT3_F

<400> SEQUENCE: 19
tactacggca acagagacg                                               19

<210> SEQ ID NO 20
<211> LENGTH: 19
<212> TYPE: DNA
<213> ORGANISM: Artificial Sequence
<220> FEATURE:
<223> OTHER INFORMATION: NT3_R

<400> SEQUENCE: 20
gttgcccaca taatcctcc                                               19

<210> SEQ ID NO 21
<211> LENGTH: 20
<212> TYPE: DNA
<213> ORGANISM: Artificial Sequence
<220> FEATURE:
<223> OTHER INFORMATION: NT4/5_F

<400> SEQUENCE: 21
ggctccatcc tgaacatcat                                              20
```

```
<210> SEQ ID NO 22
<211> LENGTH: 20
<212> TYPE: DNA
<213> ORGANISM: Artificial Sequence
<220> FEATURE:
<223> OTHER INFORMATION: NT4/5_R

<400> SEQUENCE: 22
gccatgatct acctgcctgt                                                   20

<210> SEQ ID NO 23
<211> LENGTH: 18
<212> TYPE: DNA
<213> ORGANISM: Artificial Sequence
<220> FEATURE:
<223> OTHER INFORMATION: NGF_F

<400> SEQUENCE: 23
agcattccct tgacacag                                                     18

<210> SEQ ID NO 24
<211> LENGTH: 18
<212> TYPE: DNA
<213> ORGANISM: Artificial Sequence
<220> FEATURE:
<223> OTHER INFORMATION: NGF_R

<400> SEQUENCE: 24
ggtctacagt gatgttgc                                                     18

<210> SEQ ID NO 25
<211> LENGTH: 22
<212> TYPE: DNA
<213> ORGANISM: Artificial Sequence
<220> FEATURE:
<223> OTHER INFORMATION: TrkB_F

<400> SEQUENCE: 25
aaggactttc atcgggaagc tg                                                22

<210> SEQ ID NO 26
<211> LENGTH: 19
<212> TYPE: DNA
<213> ORGANISM: Artificial Sequence
<220> FEATURE:
<223> OTHER INFORMATION: TrkB_R

<400> SEQUENCE: 26
tcgccctcca cacagacac                                                    19
```